US010285805B2

(12) United States Patent
de Juan, Jr. et al.

(10) Patent No.: US 10,285,805 B2
(45) Date of Patent: May 14, 2019

(54) ACCOMMODATING INTRAOCULAR LENS

(71) Applicant: ForSight Labs, LLC, Menlo Park, CA (US)

(72) Inventors: Eugene de Juan, Jr., Menlo Park, CA (US); Cary J. Reich, Menlo Park, CA (US); Hanson S. Gifford, III, Menlo Park, CA (US); Guy Oren, Menlo Park, CA (US); Matthew Clarke, Menlo Park, CA (US); Jose D. Alejandro, Menlo Park, CA (US)

(73) Assignee: ForSight Labs, LLC, Brisbane, CA (US)

( * ) Notice: Subject to any disclaimer, the term of this patent is extended or adjusted under 35 U.S.C. 154(b) by 0 days.

(21) Appl. No.: 15/300,116

(22) PCT Filed: Mar. 25, 2015

(86) PCT No.: PCT/US2015/022501
§ 371 (c)(1),
(2) Date: Sep. 28, 2016

(87) PCT Pub. No.: WO2015/148673
PCT Pub. Date: Oct. 1, 2015

(65) Prior Publication Data
US 2017/0181850 A1 Jun. 29, 2017

Related U.S. Application Data

(60) Provisional application No. 61/972,183, filed on Mar. 28, 2014, provisional application No. 61/977,568, filed on Apr. 9, 2014.

(51) Int. Cl.
A61F 2/16 (2006.01)
A61F 9/00 (2006.01)
A61F 9/008 (2006.01)

(52) U.S. Cl.
CPC .......... *A61F 2/1635* (2013.01); *A61F 2/1613* (2013.01); *A61F 9/0017* (2013.01);
(Continued)

(58) Field of Classification Search
CPC .... A61F 2/1635; A61F 2/1613; A61F 2/1624; A61F 9/0017; A61F 9/0026;
(Continued)

(56) References Cited

U.S. PATENT DOCUMENTS 4,159,546 A 7/1979 Shearing
4,373,218 A 2/1983 Schachar
(Continued)

FOREIGN PATENT DOCUMENTS

CA 2944010 A1 10/2015
CN 101795642 A 8/2010
(Continued)

*Primary Examiner* — Paul B Prebilic
(74) *Attorney, Agent, or Firm* — Mintz Levin Cohn Ferris Glovsky and Popeo, P.C.

(57) ABSTRACT

Disclosed is an accommodating intraocular lens device for treatment of an eye including a stabilization haptic (120) configured to be positioned within a region of an eye and a lens body having a sealed chamber containing a fixed volume of optical fluid. The lens body includes a shape changing membrane (145) configured to outwardly bow in a region surrounding the optical axis of the eye; a shape deformation membrane configured to undergo displacement relative to the first shape changing membrane; and a static element (150). An inner surface of the shape changing membrane, an inner surface of the shape deformation membrane and an inner surface of the static element collectively form the sealed chamber. The lens device also includes a force translation arm (115) having a first end configured to contact an outer surface of the shape deformation membrane of the lens body and a second end configured to engage a ciliary structure of the eye. The force translation arm is
(Continued)

configured to move relative to the lens body upon movement of the ciliary structure.

16 Claims, 18 Drawing Sheets

(52) U.S. Cl.
CPC .............. *A61F 9/0026* (2013.01); *A61F 2/16* (2013.01); *A61F 2/1624* (2013.01); *A61F 9/0008* (2013.01); *A61F 2002/1681* (2013.01); *A61F 2002/1682* (2015.04); *A61F 2009/0087* (2013.01)

(58) Field of Classification Search
CPC ............ A61F 9/0008; A61F 2210/0057; A61F 2250/0009; A61F 2250/001; A61F 2250/0013; A61F 2250/0018; A61F 2250/0091
See application file for complete search history.

(56) References Cited

U.S. PATENT DOCUMENTS

| | | |
|---|---|---|
| 4,685,921 A | 8/1987 | Peyman |
| 4,731,078 A | 3/1988 | Stoy et al. |
| 4,734,095 A | 3/1988 | Siepser |
| 4,769,035 A | 9/1988 | Kelman |
| 4,782,820 A | 11/1988 | Woods |
| 4,787,903 A | 11/1988 | Grendahl |
| 4,816,030 A | 3/1989 | Robinson |
| 4,816,031 A | 3/1989 | Pfoff |
| 4,842,601 A | 6/1989 | Smith |
| 4,865,601 A | 9/1989 | Caldwell et al. |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,957,505 A | 9/1990 | McDonald |
| 5,066,301 A | 11/1991 | Wiley |
| 5,171,266 A | 12/1992 | Wiley et al. |
| RE34,424 E | 10/1993 | Walman |
| 5,275,623 A | 1/1994 | Sarfarazi |
| 5,288,293 A | 2/1994 | O'Donnell, Jr. |
| 5,443,506 A | 8/1995 | Garabet |
| 5,489,302 A | 2/1996 | Skottun |
| 5,607,472 A | 3/1997 | Thompson |
| 5,684,637 A | 11/1997 | Floyd |
| 5,766,245 A | 6/1998 | Fedorov et al. |
| 5,774,273 A | 6/1998 | Bornhorst |
| 5,800,806 A | 9/1998 | Yamamoto |
| 5,932,205 A | 8/1999 | Wang et al. |
| 6,013,101 A | 1/2000 | Israel |
| 6,027,531 A | 2/2000 | Tassignon |
| 6,096,078 A | 8/2000 | McDonald |
| 6,117,171 A | 9/2000 | Skottun |
| 6,120,538 A | 9/2000 | Rizzo, III et al. |
| 6,143,315 A | 11/2000 | Wang et al. |
| 6,188,526 B1 | 2/2001 | Sasaya et al. |
| 6,228,115 B1 | 5/2001 | Hoffmann et al. |
| 6,261,321 B1 | 7/2001 | Kellan |
| 6,277,146 B1 | 8/2001 | Peyman et al. |
| 6,299,641 B1 | 10/2001 | Woods |
| 6,387,126 B1 | 5/2002 | Cumming |
| 6,443,985 B1 | 9/2002 | Woods |
| 6,450,642 B1 | 9/2002 | Jethmalani et al. |
| 6,493,151 B2 | 12/2002 | Schachar |
| 6,506,212 B2 | 1/2003 | Zhou et al. |
| 6,552,860 B1 | 4/2003 | Alden |
| 6,558,420 B2 | 5/2003 | Green |
| 6,592,621 B1 | 7/2003 | Domino |
| 6,645,246 B1 | 11/2003 | Weinschenk, III et al. |
| 6,730,123 B1 | 5/2004 | Klopotek |
| 6,733,122 B1 | 5/2004 | Feurer et al. |
| 6,749,634 B2 | 6/2004 | Hanna |
| 6,818,017 B1 | 11/2004 | Shu |
| 6,836,374 B2 | 12/2004 | Esch et al. |
| 6,849,091 B1 | 2/2005 | Cumming |
| 6,851,804 B2 | 2/2005 | Jethmalani et al. |
| 6,855,164 B2 | 2/2005 | Glazier |
| 6,860,601 B2 | 3/2005 | Shadduck |
| 6,930,838 B2 | 8/2005 | Schachar |
| 6,935,743 B2 | 8/2005 | Shadduck |
| 6,966,049 B2 | 11/2005 | Lepejian et al. |
| 6,966,649 B2 | 11/2005 | Shadduck |
| 7,008,449 B2 | 3/2006 | Willis et al. |
| 7,025,783 B2 | 4/2006 | Brady et al. |
| 7,060,094 B2 | 6/2006 | Shahinpoor et al. |
| 7,068,439 B2 | 6/2006 | Esch et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,217,288 B2 | 5/2007 | Esch et al. |
| 7,220,279 B2 | 5/2007 | Nun |
| 7,229,476 B2 | 6/2007 | Azar |
| 7,247,168 B2 | 7/2007 | Esch et al. |
| 7,256,943 B1 | 8/2007 | Kobrin et al. |
| 7,261,737 B2 | 8/2007 | Esch et al. |
| 7,278,739 B2 | 10/2007 | Shadduck |
| 7,293,873 B2 | 11/2007 | Dai et al. |
| 7,341,599 B1 | 3/2008 | Peyman |
| 7,369,321 B1 | 5/2008 | Ren et al. |
| 7,381,221 B2 | 6/2008 | Lang et al. |
| 7,384,429 B2 | 6/2008 | Hanna |
| 7,438,723 B2 | 10/2008 | Esch |
| 7,453,646 B2 | 11/2008 | Lo |
| 7,485,144 B2 | 2/2009 | Esch |
| 7,601,169 B2 | 10/2009 | Phillips |
| 7,615,056 B2 | 11/2009 | Ayton et al. |
| 7,637,947 B2 | 12/2009 | Smith et al. |
| 7,675,686 B2 | 3/2010 | Lo et al. |
| 7,713,299 B2 | 5/2010 | Brady et al. |
| 7,753,953 B1 | 7/2010 | Yee |
| 7,763,069 B2 | 7/2010 | Brady et al. |
| 7,776,088 B2 | 8/2010 | Shadduck |
| 7,854,764 B2 | 12/2010 | Ben Nun |
| 7,857,850 B2 | 12/2010 | Mentak et al. |
| 7,883,540 B2 | 2/2011 | Niwa et al. |
| 7,985,253 B2 | 7/2011 | Cumming |
| 7,988,285 B2 | 8/2011 | Sandstedt et al. |
| 8,018,658 B2 | 9/2011 | Lo |
| 8,034,106 B2 | 10/2011 | Mentak et al. |
| 8,158,712 B2 | 4/2012 | Your |
| 8,314,927 B2 | 11/2012 | Choi et al. |
| 8,343,216 B2 | 1/2013 | Brady et al. |
| 8,377,125 B2 | 2/2013 | Kellan |
| 8,414,646 B2 | 4/2013 | De Juan, Jr. et al. |
| 8,663,235 B2 | 3/2014 | Tassignon |
| 8,668,734 B2 | 3/2014 | Hildebrand et al. |
| 8,851,670 B2 | 10/2014 | Dai et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,974,526 B2 | 3/2015 | Bogaert |
| 9,005,282 B2 | 4/2015 | Chang et al. |
| 9,044,317 B2 | 6/2015 | Hildebrand et al. |
| 9,114,005 B2 | 8/2015 | Simonov et al. |
| 9,326,846 B2 | 5/2016 | Devita Gerardi et al. |
| 9,421,089 B2 | 8/2016 | Zadno-Azizi |
| 9,872,763 B2 * | 1/2018 | Smiley ................. A61F 2/1635 |
| 2001/0001836 A1 | 5/2001 | Cumming |
| 2003/0060878 A1 | 3/2003 | Shadduck |
| 2003/0149480 A1 | 8/2003 | Shadduck |
| 2003/0171809 A1 | 9/2003 | Phillips |
| 2003/0187504 A1 | 10/2003 | Weinschenk et al. |
| 2004/0006387 A1 | 1/2004 | Kelman |
| 2004/0034417 A1 | 2/2004 | Heyman |
| 2004/0039446 A1 | 2/2004 | McNicholas |
| 2004/0082993 A1 | 4/2004 | Woods |
| 2004/0082995 A1 | 4/2004 | Woods |
| 2004/0111153 A1 | 6/2004 | Woods et al. |
| 2004/0162612 A1 | 8/2004 | Portney et al. |

(56) References Cited

U.S. PATENT DOCUMENTS

| | | |
|---|---|---|
| 2004/0169816 A1* | 9/2004 | Esch .................... A61F 2/1616 351/159.02 |
| 2004/0169820 A1 | 9/2004 | Dai et al. |
| 2004/0237971 A1 | 12/2004 | Radhakrishnan et al. |
| 2005/0021138 A1 | 1/2005 | Woods |
| 2005/0060032 A1 | 3/2005 | Magnante et al. |
| 2005/0065534 A1 | 3/2005 | Hohl |
| 2005/0107873 A1 | 5/2005 | Zhou |
| 2005/0113914 A1 | 5/2005 | Miller et al. |
| 2005/0125059 A1 | 6/2005 | Pinchuk et al. |
| 2005/0137703 A1 | 6/2005 | Chen |
| 2005/0251253 A1 | 11/2005 | Gross |
| 2006/0047340 A1 | 3/2006 | Brown |
| 2006/0064162 A1 | 3/2006 | Klima |
| 2006/0100701 A1 | 5/2006 | Esch et al. |
| 2006/0259138 A1 | 11/2006 | Peyman |
| 2007/0010881 A1 | 1/2007 | Soye et al. |
| 2007/0054131 A1 | 3/2007 | Stewart |
| 2007/0088433 A1 | 4/2007 | Esch et al. |
| 2007/0100444 A1 | 5/2007 | Brady et al. |
| 2007/0123982 A1 | 5/2007 | Yablonski et al. |
| 2007/0129798 A1 | 6/2007 | Chawdhary |
| 2007/0129800 A1 | 6/2007 | Cumming |
| 2008/0046075 A1 | 2/2008 | Esch et al. |
| 2008/0046076 A1 | 2/2008 | Rombach |
| 2008/0097459 A1 | 4/2008 | Kammerlander et al. |
| 2008/0103592 A1 | 5/2008 | Maloney |
| 2008/0106698 A1 | 5/2008 | Dai et al. |
| 2008/0119864 A1 | 5/2008 | Deinzer et al. |
| 2008/0125862 A1 | 5/2008 | Blake |
| 2008/0129962 A1 | 6/2008 | Dai et al. |
| 2008/0288066 A1 | 11/2008 | Cumming |
| 2009/0005865 A1* | 1/2009 | Smiley .................... A61F 2/1613 623/6.13 |
| 2009/0012609 A1 | 1/2009 | Geraghty et al. |
| 2009/0171458 A1 | 7/2009 | Kellan et al. |
| 2009/0234449 A1 | 9/2009 | De Juan, Jr. et al. |
| 2009/0292355 A1 | 11/2009 | Boyd et al. |
| 2010/0094415 A1 | 4/2010 | Bumbalough |
| 2010/0121444 A1 | 5/2010 | Ben Nun |
| 2011/0054600 A1 | 3/2011 | Bumbalough |
| 2011/0071628 A1 | 3/2011 | Gross et al. |
| 2011/0118834 A1 | 5/2011 | Lo et al. |
| 2012/0253459 A1* | 10/2012 | Reich .................... A61F 2/1635 623/6.46 |
| 2013/0110235 A1 | 5/2013 | Schwiegerling |
| 2013/0116781 A1 | 5/2013 | Ben Nun |
| 2013/0245754 A1 | 9/2013 | Blum et al. |
| 2014/0012240 A1 | 1/2014 | Ho et al. |
| 2014/0058507 A1 | 2/2014 | Reich et al. |
| 2014/0228949 A1 | 8/2014 | Argento et al. |
| 2015/0257874 A1 | 9/2015 | Hildebrand et al. |

FOREIGN PATENT DOCUMENTS

| | | |
|---|---|---|
| CN | 103025271 A | 4/2013 |
| CN | 103096837 A | 5/2013 |
| EP | 1917932 A1 | 5/2008 |
| EP | 1932492 A1 | 6/2008 |
| JP | 2005-169131 A | 6/2005 |
| JP | 2005-533611 A | 11/2005 |
| JP | 2008-532617 A | 8/2008 |
| JP | 2009-532176 A | 9/2009 |
| JP | 2011-500270 A | 1/2011 |
| WO | WO-03/000154 A2 | 1/2003 |
| WO | WO-03/017867 A2 | 3/2003 |
| WO | WO-2004/010905 A2 | 2/2004 |
| WO | WO-2004/037122 A2 | 5/2004 |
| WO | WO-2004/037127 A2 | 5/2004 |
| WO | WO-2004/053568 A1 | 6/2004 |
| WO | WO-2004/107024 A1 | 12/2004 |
| WO | WO-2005/057272 A2 | 6/2005 |
| WO | WO-2005/082285 A1 | 9/2005 |
| WO | WO-2007/113832 A2 | 10/2007 |
| WO | WO-2007/117476 A2 | 10/2007 |
| WO | WO-2008/031231 A1 | 3/2008 |
| WO | WO-2009/055099 A1 | 4/2009 |
| WO | WO-2010/010565 A2 | 1/2010 |
| WO | WO-2012/006186 A2 | 1/2012 |
| WO | WO-2012/023133 A1 | 2/2012 |
| WO | WO-2012/067994 A2 | 5/2012 |
| WO | WO-2013/016804 A1 | 2/2013 |

* cited by examiner

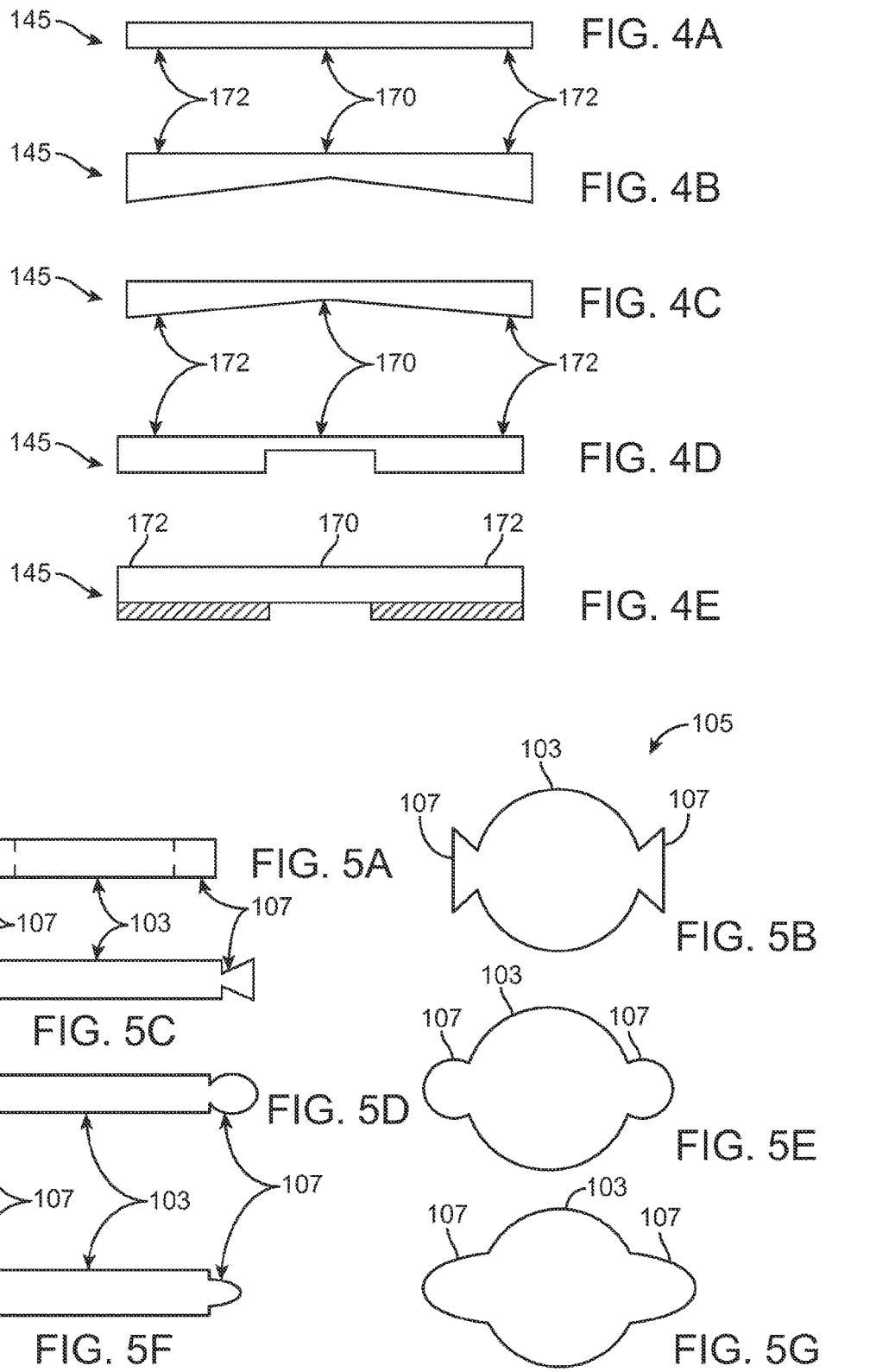

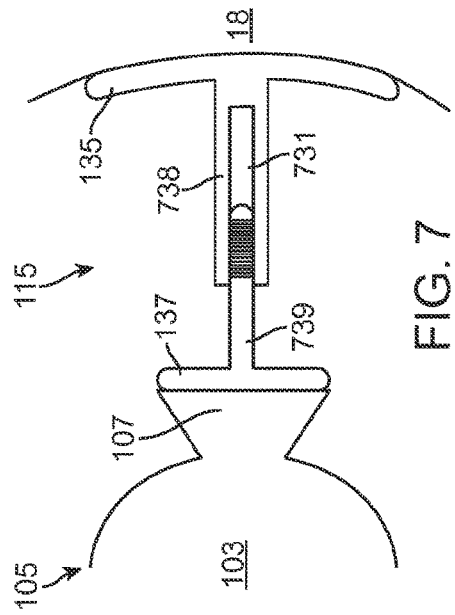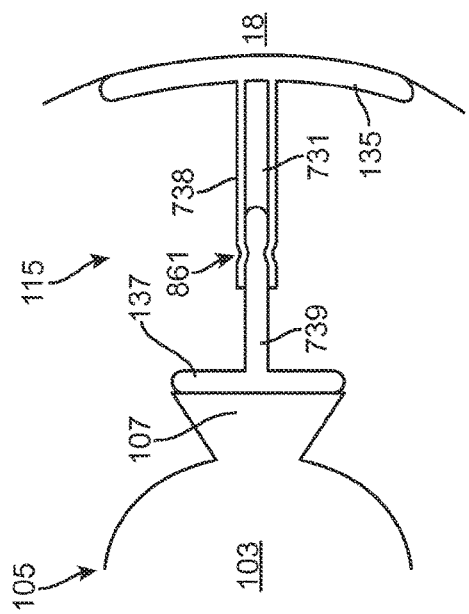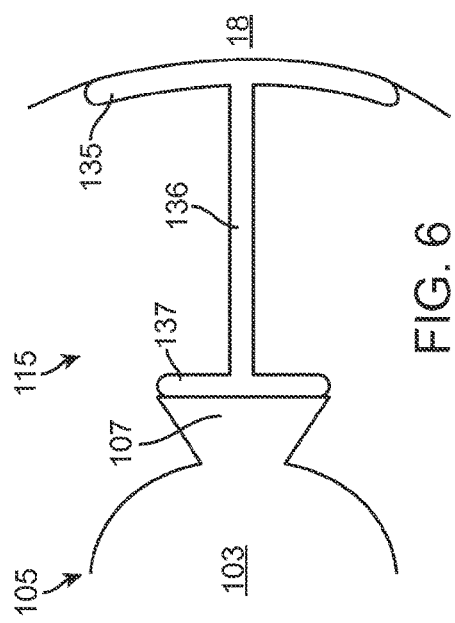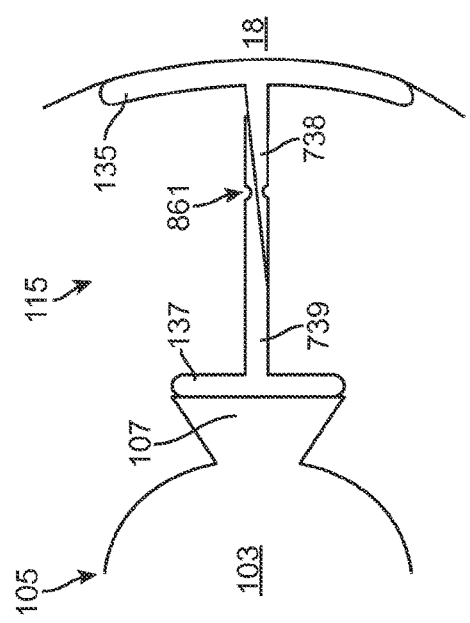

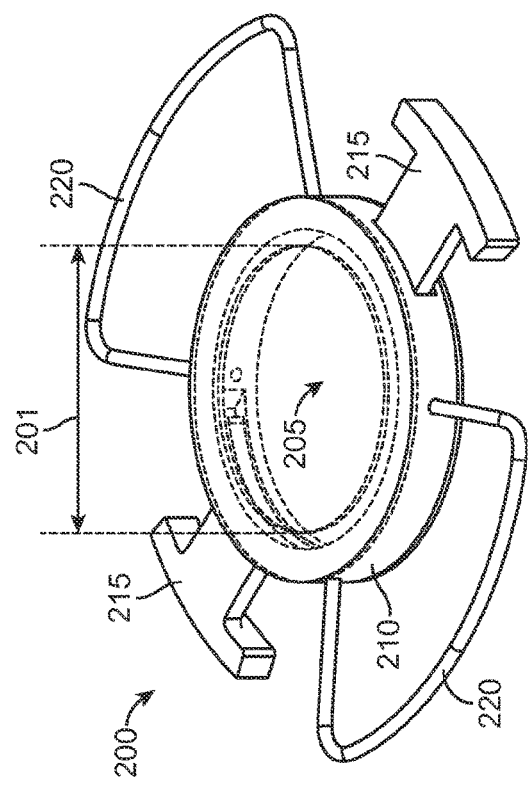
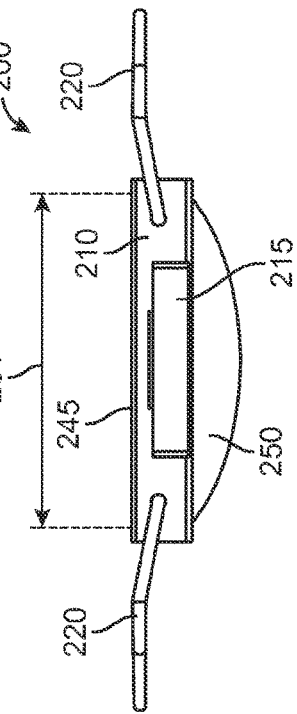
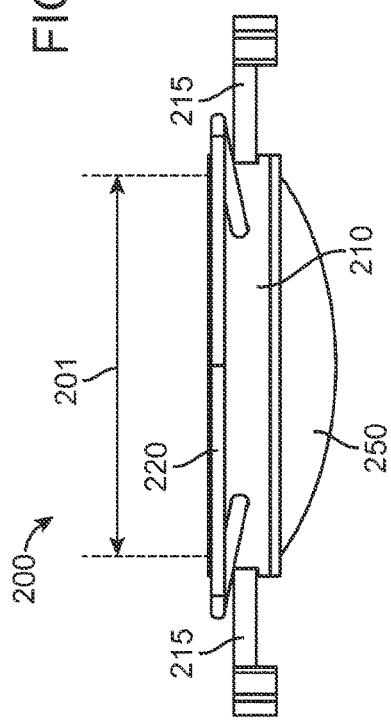
FIG. 25A
FIG. 25B
FIG. 25C

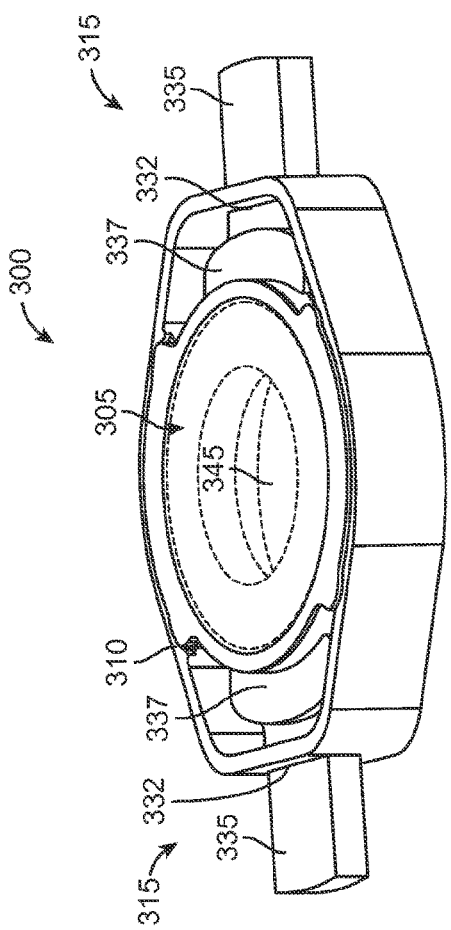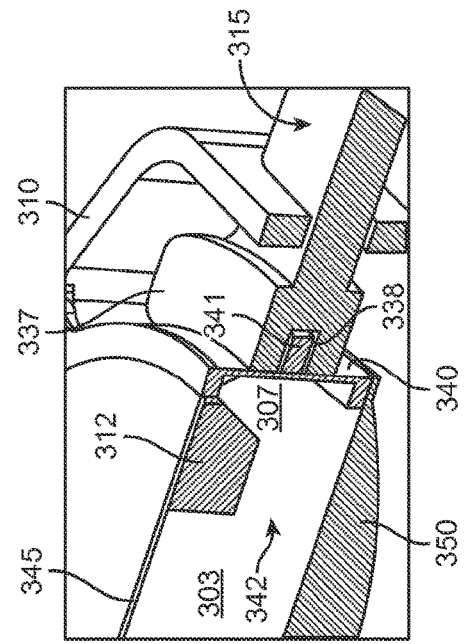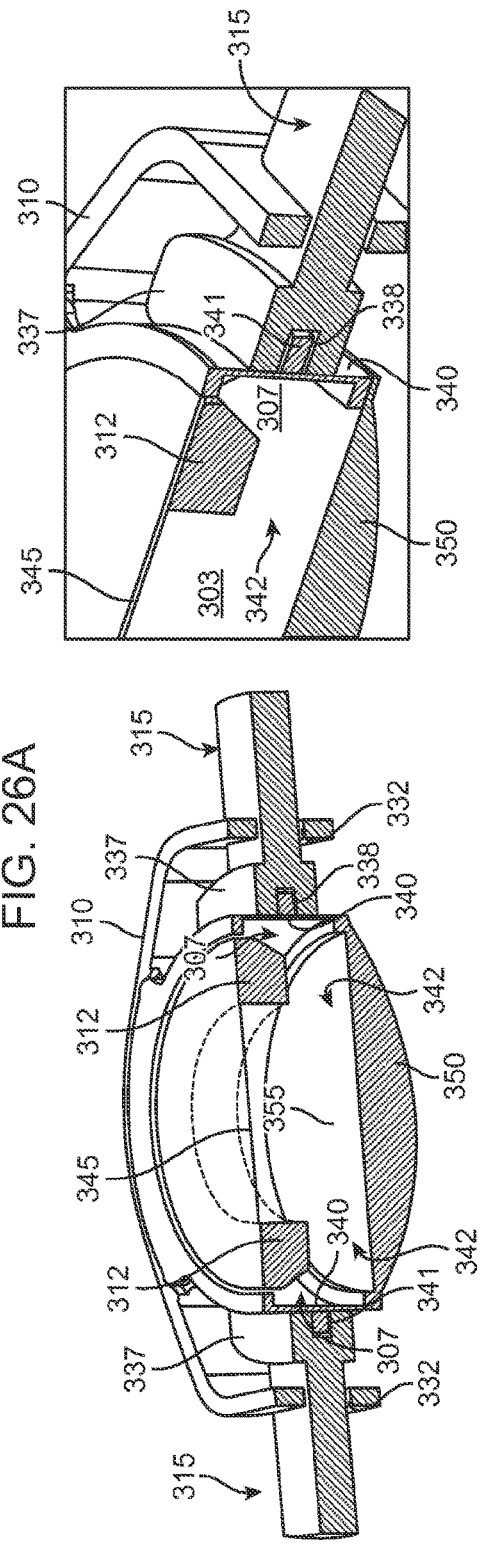

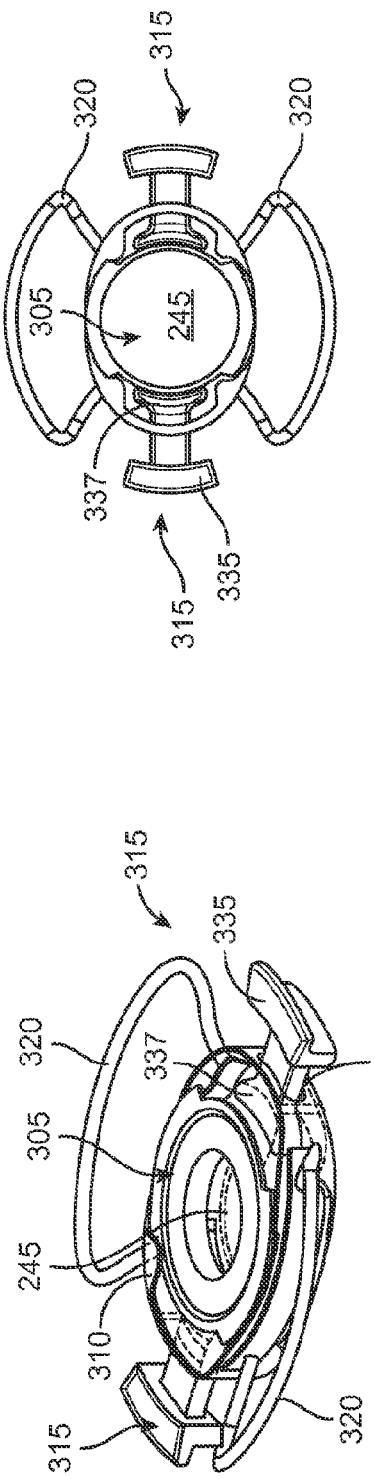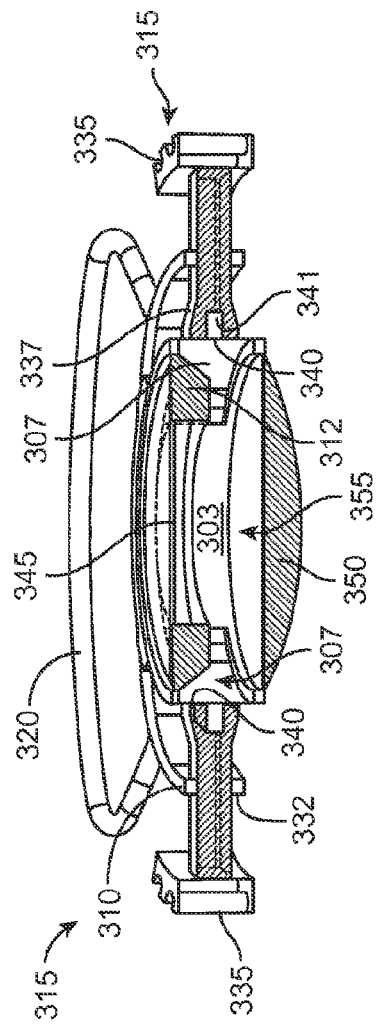
FIG. 26E
FIG. 26F
FIG. 26D

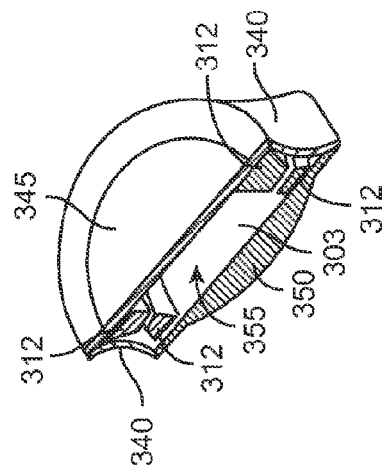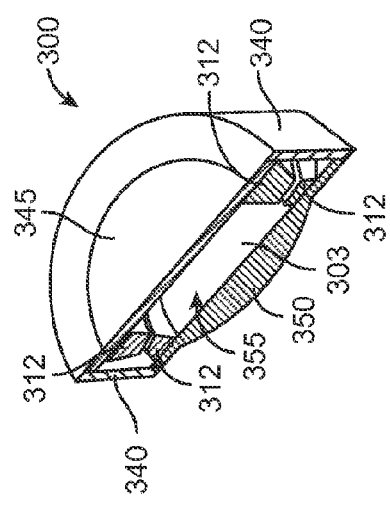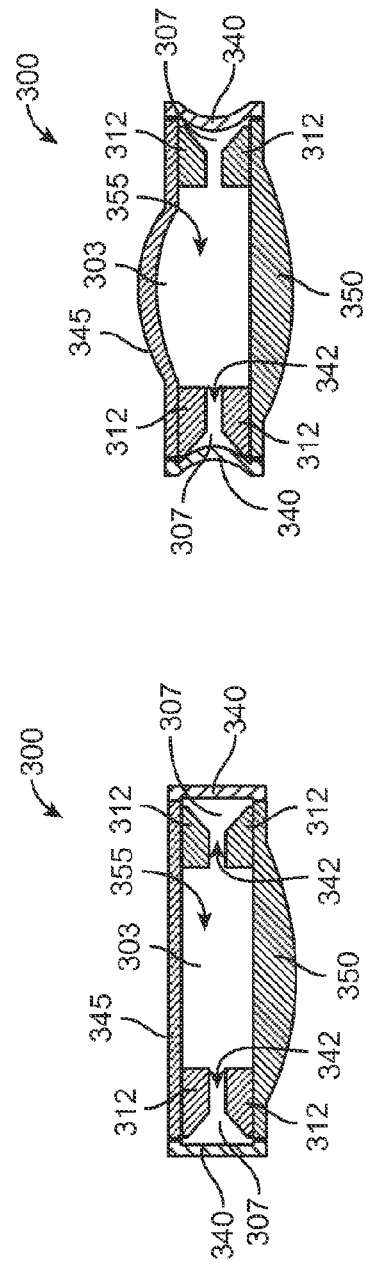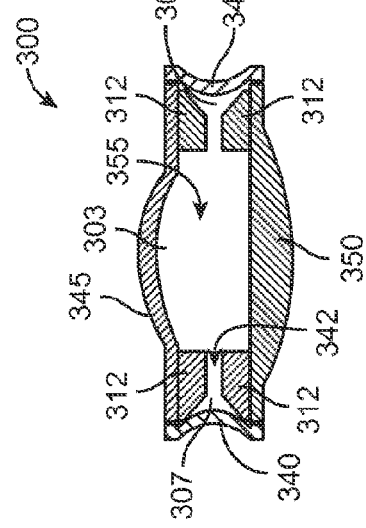

ACCOMMODATING INTRAOCULAR LENS

CROSS-REFERENCE TO PRIORITY DOCUMENTS

The present application is a national-phase entry of Patent Cooperation Treaty Application No. PCT/US2015/022501, which has an international filing date of Mar. 25, 2015, and claims the benefit of priority to U.S. Provisional Application Ser. No. 61/972,183, filed Mar. 28, 2014 and U.S. Provisional Application Ser. No. 61/977,568, filed Apr. 9, 2014; the full disclosures of which are incorporated herein by reference in their entireties.

BACKGROUND

The present disclosure relates generally to the field of ophthalmics, more particularly to ophthalmic devices, including intraocular lenses (IOLs) such as accommodating intraocular lenses.

A healthy young human eye can focus an object in far or near distance, as required. The capability of the eye to change back and forth from near vision to far vision is called accommodation. Accommodation occurs when the ciliary muscle contracts to thereby release the resting zonular tension on the equatorial region of the capsular bag. The release of zonular tension allows the inherent elasticity of the lens to alter to a more globular or spherical shape, with increased surface curvatures of both the anterior and posterior lenticular surfaces.

The human lens can be afflicted with one or more disorders that degrade its functioning in the vision system. A common lens disorder is a cataract which is the opacification of the normally clear, natural crystalline lens matrix. The opacification can result from the aging process but can also be caused by heredity or diabetes. In a cataract procedure, the patient's opaque crystalline lens is replaced with a clear lens implant or IOL.

In conventional extracapsular cataract surgery, the crystalline lens matrix is removed leaving intact the thin walls of the anterior and posterior capsules together with zonular ligament connections to the ciliary body and ciliary muscles. The crystalline lens core is removed by phacoemulsification through a curvilinear capsularhexis i.e., the removal of an anterior portion of the capsular sac.

After a healing period of a few days to weeks, the capsular sac effectively shrink-wraps around the IOL due to the capsularhexis, the collapse of the walls of the sac and subsequent fibrosis. Cataract surgery as practiced today causes the irretrievable loss of most of the eye's natural structures that provide accommodation. The crystalline lens matrix is completely lost and the integrity of the capsular sac is reduced by the capsularhexis. The "shrink-wrap" of the capsular sac around the IOL can damage the zonule complex, and thereafter the ciliary muscles may atrophy. Thus, conventional IOL's, even those that profess to be accommodative, may be unable to provide sufficient axial lens spatial displacement along the optical axis or lens shape change to provide an adequate amount of accommodation for near vision.

It is known to implant a combination of lenses to address refraction errors in the existing lens in the case of phakic IOLs or improve the refractive results of standard IOL after cataract surgery in the case of pseudophakic patients. These "piggyback" IOLs can be placed anterior to the previously implanted IOL or natural lens to improve the refractive results of cataract surgery in the case of pseudophakes or to change the refractive status of the eye in the case of phakic eyes, usually to correct high myopia. Generally, these lenses are implanted in the sulcus and are non-accommodating.

SUMMARY

In some implementations, disclosed is an accommodating intraocular lens device for treatment of an eye. The lens device includes a stabilization haptic configured to be positioned within a region of an eye. The lens device includes a lens body having a sealed chamber containing a fixed volume of optical fluid. The lens body includes a shape changing membrane configured to outwardly bow in a region surrounding the optical axis of the eye; a shape deformation membrane configured to undergo displacement relative to the first shape changing membrane; and a static element. An inner surface of the shape changing membrane, an inner surface of the shape deformation membrane and an inner surface of the static element collectively form the sealed chamber. The lens device also includes a force translation arm having a first end configured to contact an outer surface of the shape deformation membrane of the lens body and a second end configured to engage a ciliary structure of the eye. The force translation arm is configured to move relative to the lens body upon movement of the ciliary structure.

The shape deformation membrane can be configured to undergo inward displacement towards the optical axis of the eye relative to the shape changing membrane during accommodation. Inward movement of the force translation arm can cause inward movement of at least one or more regions of the shape deformation membrane towards the optical axis of the eye causing a deformation of the sealed chamber. Inward movement of the shape deformation membrane can cause the optical fluid in the sealed chamber to press against the inner surface of the shape changing membrane and causes outward bowing of the shape changing membrane. The lens device can further include an internal support located within the sealed chamber. The internal support can mechanically isolate optical components of the lens from distortion during movement of the force translation arm. The internal support can include a plurality of internal supports spaced apart from one another within the sealed chamber. The internal support can include a tapered geometry to avoid contact during inward movement of the shape deformation membrane.

The stabilization haptic can be bonded to the lens body. The stabilization haptic can be molded as part of the lens body. The lens device can further include an exterior support. The internal support can be coupled to a perimeter region of the shape changing membrane. The internal support can form a partition within the sealed chamber dividing the sealed chamber into a deformable region and a central region. The deformable region can be located outside an optic zone. The deformable region can be located inside an optic zone. Inward movement of the force translation arm can cause inward movement of the shape deformation membrane and a deformation of the deformable region. Inward movement of the shape deformation membrane can compress the sealed chamber. The optical fluid in the sealed chamber can be non-compressible and can press against the inner surface of the shape changing membrane and cause outward bowing of the shape changing membrane. The internal support can be further coupled to a region of the static element. The internal support can include a channel extending through the internal support providing fluid communication between the deformable region and the central region of the sealed chamber.

The lens device can further include an exterior support. The exterior support can be rigid and can be configured to prevent distortion caused by movement of the force translation arms relative to the lens body. The stabilization haptic can be bonded to an external surface of the exterior support. The stabilization haptic can be molded as part of the exterior support. The first end of the force translation arm can extend through a channel in a peripheral wall of the exterior support such that the first end is positioned against the shape deformation membrane. The exterior support can include a central annular region and opposed side regions. The lens body can include a central portion and opposed, deformable portions. The central portion can align with the central annular region of the exterior support and the deformable portions of the lens body extend within the opposed side regions of the exterior support. An outer surface of the shape deformation membrane can be exposed through the central annular region. An outer surface of the static element can be exposed through the central annular region. A first of the force translation arms can extend through a first opening in a first sidewall of the exterior support into a first channel. A second of the force translation arms can extend through a second opening in a second sidewall of the exterior support into a second channel. The first channel and the second channel can be on opposite sides of the central annular region. The force translation arms can be configured to move back and forth within the first and second channels.

The shape deformation membrane can have a first surface coupled to the shape changing membrane and a second surface coupled to the static element and a sidewall extending between the first surface and the second surface. The sidewall of the shape deformation membrane can be aligned with and bonded to an inner surface of the central region of the exterior support such that the lens body is fixedly positioned relative to the exterior support. The central portion can surround the optical axis and deformable portions are located outside the central portion. An outer surface of the shape changing membrane near the central portion can be aligned with and bonded to an inner surface of the central annular region of the exterior support. The deformable portions can be freely movable within the exterior support. The deformable portions can be configured to undergo inward, collapsible movement or displacement relative to the central portion during accommodation. The first ends of the force translation arms cam be configured to be positioned against the deformable portions. Upon contraction, the ciliary structure can press against the second ends causing the first ends of the force translation arms to press upon the deformable portions and cause inward, collapsible movement of the deformable portions towards the central portion. Inward, collapsible movement of the deformable portions towards the central portion can cause the region of the shape changing membrane to outwardly bow. Inward, collapsible movement of the deformable portions towards the central portion can cause the optical fluid in the sealed chamber to press against the inner surface of the shape changing membrane causing the outward bowing of the shape changing membrane.

The central portion of the lens body can be generally circular and the deformable portions of the lens body have a shape selected from the group consisting of bellowed, pleated, trapezoidal, cylindrical, elliptical, conical, spherical, and hemi-spherical. The deformable portions of the lens body can move relative to the central portion of the lens body in response to a force applied by the ciliary structure onto the force translation arms. The deformable portions can move a distance between about 50 um and about 500 um. The distance the deformable portions move can cause at least a change in power of the lens body by at least 3 diopters. The force applied can be between about 0.1 gf to about 5 gf. The stabilization haptic can be configured to maintain alignment of the optics and resist movement of the device following implantation in the eye. The stabilization haptic can further include a biting element to improve fixation of the haptic within the eye. The biting element can include a grooved edge and/or a hole. The stabilization haptic can be open-loop, closed-loop, plate-style, plate loop, monobloc-plate style, j-loop, c-loop, modified J-loop, multi-piece, single-piece, angulated, planar, or offset haptics. The stabilization haptic can be coaxial or coplanar with the force translation arms. The stabilization haptic can be positioned on a different plane than the force translation arms. The stabilization haptic can be flexible, foldable or formed of a shape memory material. The stabilization haptic can be positioned within a ciliary sulcus or the capsular bag of the eye.

The lens body can include a deformable portion that is located outside the optic zone. The deformable portion can be a region of the shape deformation membrane. The lens body can include a deformable portion that is located inside the optic zone. The deformable portion can be a region of the shape deformation membrane. The shape deformation membrane can be annular. Outward bowing of the shape changing membrane can be manually adjustable after implantation of the device in the eye. The static element can be a static lens having an optical power. The static lens can be positioned posteriorly relative to the eye and the shape changing member can be positioned anteriorly relative to the eye. The shape changing membrane can have a constant thickness. The region of the shape changing membrane can be a reduced thickness region prone to give way upon increased internal pressure within the sealed chamber or upon application of pressure by the optical fluid against the inner surface of the shape changing membrane. The optical fluid can include a non-compressible liquid or gel of high clarity and transmission in the visible spectrum. The optical fluid can be silicone oil or fluorosilicone oil.

The force translation arms can have a length configured to extend between the shape deformation membrane of the lens body and the ciliary structure. The length can be adjustable prior to insertion of the device in the eye or after insertion of the device in the eye. The adjustment can be mechanical. The force translation arms can include two portions coupled together. The two portions can be coupled together by a hinge, piston, crimp, threads, or cam mechanism. The two portions can be coupled together by a chemical material. The ciliary structure can include at least one of ciliary muscle, ciliary body, ciliary process, and zonules.

More details of the devices, systems and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIGS. 4A-4E are various schematic side views of a shape changing membrane;

FIG. 5A is a schematic cross-sectional view of an implementation of a lens body and FIG. 5B is a schematic, top plan view of the lens body of FIG. 5A;

FIG. 5C is a schematic cross-sectional view of another implementation of a lens body;

FIG. 5D is a schematic cross-sectional view of an implementation of a lens body and FIG. 5E is a schematic, top plan view of the lens body of FIG. 5D;

FIG. 5F is a schematic cross-sectional view of an implementation of a lens body and FIG. 5G is a schematic, top plan view of the lens body of FIG. 5F;

FIG. 6 is a schematic top plan view of an implementation of a force translation arm extending between a ciliary structure and a lens body;

FIG. 7 is a schematic top plan view of an implementation of a force translation arm extending between a ciliary structure and a lens body;

FIG. 8A is a schematic top plan view of an implementation of a force translation arm extending between a ciliary structure and a lens body;

FIG. 8B is a schematic top plan view of an implementation of a force translation arm extending between a ciliary structure and a lens body;

FIG. 25A is a perspective view of another implementation of an accommodating intraocular lens;

FIGS. 25B and 25C are side views of the lens of FIG. 25A;

FIG. 26A is a perspective view of another implementation of an accommodating intraocular lens;

FIG. 26B is a cross-sectional view of the lens of FIG. 26A;

FIG. 26C is a detailed view of FIG. 26B;

FIG. 26D is a perspective view of an accommodating intraocular lens;

FIG. 26E is a top view of the lens of FIG. 26D;

FIG. 26F is a cross-sectional side view of the lens of FIG. 26D;

FIGS. 27A and 27C are cross-sectional partial perspective views of another implementation of an accommodating intraocular lens in a disaccommodated, relaxed state and an accommodated, actuated state, respectfully;

FIGS. 27B and 27D are cross-sectional partial side views of the lens of FIGS. 27A and 27C in a disaccommodated, relaxed state and an accommodated, actuated state, respectfully.

It should be appreciated that the drawings herein are exemplary only and are not meant to be to scale.

DETAILED DESCRIPTION

The present disclosure relates generally to the field of ophthalmics, more particularly to ophthalmic devices, including intraocular lenses (IOLs) such as accommodating intraocular lenses (AIOLs). The devices described herein can be switched back and forth repeatedly between accommodation to disaccommodation, just as in a young accommodative natural eye. The devices described herein can provide focusing power in both the distance and accommodative ranges by mechanically and functionally interacting with eye tissues typically used by a natural lens such as the ciliary body, ciliary processes, and the zonules, to effect accommodation and disaccommodation. The forces generated by these tissues are functionally translated to the devices described herein causing a power change to more effectively accommodate. The devices described herein are configured to be adjusted for size and fit prior to, during, as well as at any time after implantation. The devices described herein can be implanted in the eye to replace a diseased, natural lens. It should be appreciated, however, the devices can also be implanted as a supplement of a natural lens (phakic patient) or an intraocular lens previously implanted within a patient's capsular bag (pseudophakic patient).

Figure 1A:
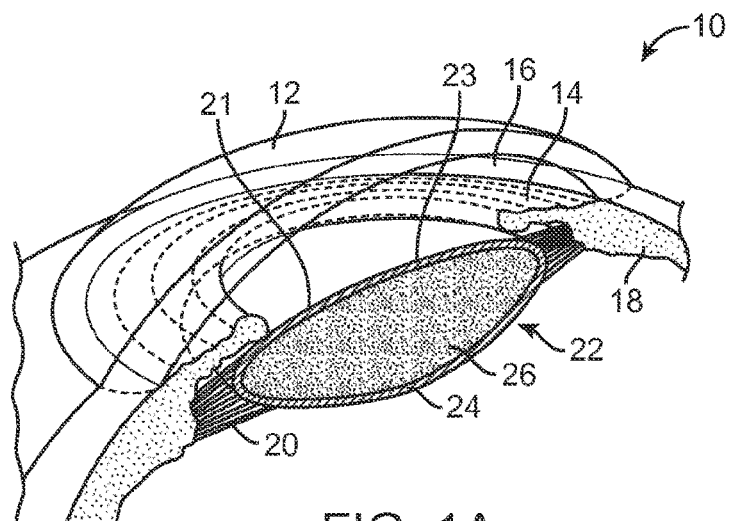
FIG. 1A is a perspective cut-away view of an eye with an opacified lens capsule.

With reference to FIG. 1A, the human eye 10 includes a cornea 12, iris 14, sulcus 16, ciliary muscle 18, zonules 20, a lens 21 contained within a capsular bag 22. Accommodation occurs when the ciliary muscle 18 contracts to thereby release the resting zonular tension on the equatorial region of the capsular bag 22. The release of zonular tension allows the inherent elasticity of the lens 21 to alter to a more globular or spherical shape, with increased surface curvatures of both the anterior lenticular surface 23 and posterior lenticular surface 24. In addition, the human lens can be afflicted with one or more disorders that degrade its functioning in the vision system. A common lens disorder is a cataract which consists of the opacification of the normally clear, natural crystalline lens matrix 26. The opacification can result from the aging process but can also be caused by heredity or diabetes. FIG. 1A shows a lens capsule comprising a capsular bag 22 with an opacified crystalline lens nucleus 26.

Figure 1B:
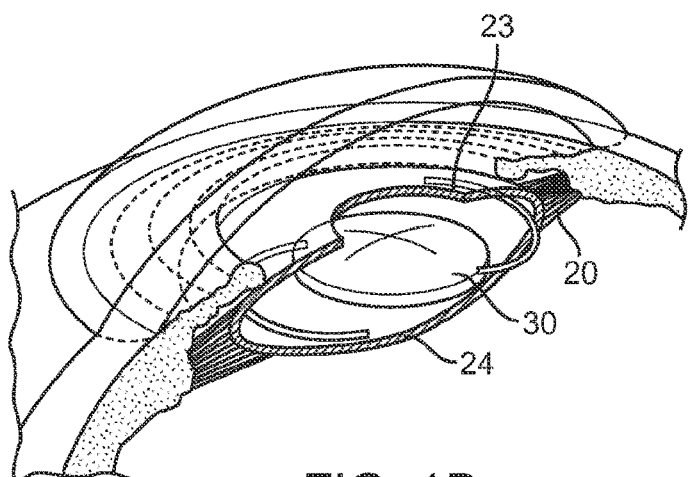
FIG. 1B is a perspective cut-away view of the eye of FIG. 1A with a curvilinear capsularhexis and the crystalline lens matrix removed with the implantation of a traditional 3-piece IOL.

In a cataract procedure, the patient's opaque crystalline lens is replaced with a clear lens implant or IOL 30. In conventional extracapsular cataract surgery as depicted in FIG. 1B, the crystalline lens matrix 26 is removed leaving intact the thin walls of the anterior and posterior capsules together with zonular ligament connections to the ciliary body and ciliary muscles 18. The crystalline lens core is removed by phacoemulsification through a curvilinear capsularhexis as illustrated in FIG. 1B, i.e., the removal of an anterior portion 23 of the capsular sac. FIG. 1B depicts a conventional 3-piece IOL 30 just after implantation in the capsular bag 22. The capsular bag 22 after a healing period of a few days to weeks can effectively shrink-wrap around a conventional 3-piece IOL 30 due to the capsularhexis, the collapse of the walls of the sac 22 and subsequent fibrosis. Cataract surgery as practiced today causes the irretrievable loss of most of the eye's natural structures that provide accommodation. The crystalline lens matrix 26 is completely lost and the integrity of the capsular sac 22 is reduced by the capsularhexis. The fibrosis of the capsular bag limits the dynamic movement of a lens placed in that bag. Thus, conventional IOL's, even those that profess to be accommodative, may be unable to provide sufficient axial lens spatial displacement along the optical axis or lens shape change to provide an adequate amount of accommodation for near vision.

Figure 1C:
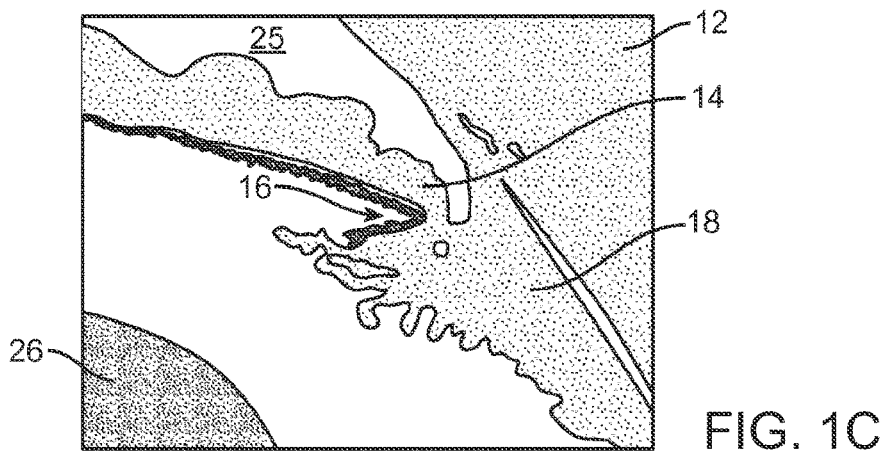
FIG. 1C is a cross-sectional view of an anterior angle of an eye.

It is known to implant a combination of lenses to address refraction errors in the existing lens in the case of phakic IOLs or improve the refractive results of standard IOL after cataract surgery in the case of pseudophakic patients. These "piggyback" IOLs can be placed anterior to the previously implanted IOL or natural lens to improve the refractive results of cataract surgery in the case of pseudophakes or to change the refractive status of the eye in the case of phakic eyes, usually to correct high myopia. Generally, these lenses are implanted in the ciliary sulcus and are non-accommodating. As best shown in FIG. 1C, the ciliary sulcus 16 is the space between the posterior surface of the base of the iris 14 and the anterior surface of the ciliary body.

Accommodating IOLs are beneficial also for patients not suffering from cataracts, but who wish to reduce their dependency on glasses and contacts to correct their myopia, hyperopia and presbyopia. Intraocular lenses used to correct large errors in myopic, hyperopic, and astigmatic eye are called "phakic intraocular lenses" and are implanted without removing the crystalline lens. In some cases, aphakic IOLs (not phakic IOLs) are implanted via lens extraction and replacement surgery even if no cataract exists. During this surgery, the crystalline lens is extracted and an IOL replaces it in a process that is very similar to cataract surgery. Refractive lens exchange, like cataract surgery, involves lens replacement, requires making a small incision in the eye for lens insertion, use of local anesthesia and lasts approximately 30 minutes. The accommodating IOLs described herein can be used in patients for refractive lens exchange.

Described herein are accommodating IOLs ("AIOLs") that can achieve the desired optical power change, for example in the range of 3 diopter (D) to about 5 D, independent of the capsular bag. The devices described herein can include one or more force translation arms configured to be positioned in the eye to harness movements of one or more ciliary structures and translate the movements into functional forces to drive shape change of the lens body for accommodation and disaccommodation. The devices described herein can further include one or more stabilization haptics that can be separate from the force translation arms and positioned, for example, within the ciliary sulcus. The devices described herein obviate known issues that tend to occur due to capsular fibrosis described above. It should be appreciated that the devices described herein can be configured to harness movements of one or combinations of ciliary structures including, but not limited to, the ciliary muscle, the ciliary body, ciliary process, and zonules. For the sake of brevity, ciliary structure is used throughout to refer to the one or more ciliary structures for which movements can be harnessed by the force translation arms to effect accommodation of the lens body as will be described in more detail herein.

The devices described herein can be implanted in the eye to replace a diseased, natural lens. In some implementations, the devices described herein can be implanted as aphakic IOLs via refractive lens exchange procedures. The intraocular lenses described herein can also be implanted as a supplement of a natural lens (phakic patient) or an intraocular lens previously implanted within a patient's capsular bag (pseudophakic patient). The lenses described herein can be used in combination with intraocular lenses described in U.S. Patent Publication Nos. 2009/0234449, 2009/0292355 and 2012/0253459, which are each incorporated by reference herein in their entirety. As such, the lenses described herein can be used independently or as so-called "piggyback" lenses. Piggyback lenses can be used to correct residual refractive errors in phakic or pseudophakic eyes. The primary IOL used to replace the natural lens is generally thicker and usually has a power that can be in the range of ±10 D to ±25 D. The thicker, larger power lenses generally do not accommodate. In contrast, the supplemental lens need not possess a full range of diopters (D). The supplemental lens can be relatively thin compared to the primary IOL and can undergo more accommodation. Shape change and movement of the thinner lens is generally more easily accomplished relative to a thick primary lens. The AIOLs described herein can be used independently and need not be used in combination as piggyback lenses with the natural lens or an implanted IOL. The AIOLs described herein can be configured to be positioned in the sulcus 16 and/or the capsular bag 22.

The devices and systems described herein can incorporate any of a variety of features described herein and that elements or features of one implementation of a device and system described herein can be incorporated alternatively or in combination with elements or features of another implementation of a device and system described herein as well as the various implants and features described in U.S. Patent Publication Nos. 2009/0234449, 2009/0292355 and 2012/0253459, which are each incorporated by reference herein in their entirety. For the sake of brevity, explicit descriptions of each of those combinations may be omitted although the various combinations are to be considered herein. Additionally, the devices and systems described herein can be positioned in the eye and need not be implanted specifically as shown in the figures or as described herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

Turning now to FIGS. 2A to 2H, the accommodating intraocular lens ("AIOL") 100 can include a lens body 105 positioned within and coupled to an exterior support 110 and having one or more force translation arms 115. One or more stabilization haptics 120 can be incorporated. The exterior support 110 can include a central annular region 125 within which a central portion 103 of the lens body 105 can be positioned and opposed, side regions 130 within which deformable portions 107 of the lens body 105 extend. An anterior surface of the lens body 105 can be exposed through an opening of the central annular region 125 of the exterior support 110 from the anterior side of the device. Similarly, a posterior surface of the lens body 105 can be exposed through the opening of the central annular region 125 of the exterior support 110 from the posterior side of the device. The opposed, side regions 130 of the exterior support 110 can each include a channel 132 extending from an opening 133 or slot through a sidewall 134 of the side regions 130 into the central annular region 125 (best shown in FIG. 2H). It should be appreciated that although two, opposing force translation arms are shown in the figures, the devices described herein can have one, two, three, four or more force translation arms 115. In some implementations, a force translation arm 115 can extend through the opening 133 of one of the side regions 130 and a second force translation arm 115 can extend through the opening 133 of the opposing side region 130. The force translation arms 115 can each include an outer, contact portion 135 configured to contact or engage at least a portion of a ciliary structure and an inner, contact portion 137 configured to contact or be positioned against at least a portion of the lens body 105. Contact portion 135 of each force translation arm 115 can remain external to the exterior support 110 such that it can remain in contact with the ciliary structure during accommodation and disaccommodation. Contact portion 137 of each force translation arm 115 can translate within channel 132 by extending through opening 133. The force translation arms 115 can move freely back and forth within channel 132 through the openings 133 as the ciliary structure moves to effect accommodative shape change of the lens body 105 as will be described in more detail below.

For example, and without limiting this disclosure to any particular theory or mode of operation, the ciliary muscle 18 is an annular structure or sphincter. In natural circumstances, when the eye is viewing an object at a far distance, the ciliary muscle 18 within the ciliary body relaxes and the inside diameter of the ciliary muscle 18 gets larger. The ciliary processes pull on the zonules 20, which in turn pull on the lens capsule 22 around its equator. This causes a natural lens to flatten or to become less convex, which is called disaccommodation. During accommodation, the ciliary muscle 18 contracts and the inside diameter of the ciliary muscle 18 gets smaller. The ciliary processes release the tension on the zonules 20 such that a natural lens will spring back into its natural, more convex shape and the eye can focus at near distances. As will be described in more detail below, the devices described herein are configured to harness that inward/anterior movement of the ciliary muscle 18 (or one or more ciliary structures) with the force translation arms 115. As will be described in more detail herein, the contact portion 135 of the force translation arms 115 can be implanted such that they are either in resting contact or readily in contact upon contraction of the ciliary muscle 18 with at least one of the ciliary structures (i.e. zonules, ciliary processes, and/or ciliary body). Contraction of the ciliary muscle and inward/anterior movement of one or more of the ciliary structures towards the optical axis applies a force against the contact portions 135 of the force translation arms 115. The force translation arms 115 transfer the force to the lens body 105 by sliding inward through channels 132 toward central annular region 125. Contact portions 137 of the force translation arms 115 are configured to abut the deformable portions 107 of the lens body 105 causing shape change in the central portion 103 of the lens body 105 into a more spherical or convex shape thereby increasing the power of the lens suitable for near vision focus.

The exterior support 110 can be formed of a biocompatible plastic, including but not limited to silicone, polydimethylsiloxane (PDMS), polyurethane, PMMA, PVDF, polyamide, polypropylene, polycarbonate, PEEK, etc. and combinations thereof. The exterior support 110 can be configured to prevent distortion caused by movement of the force translation arms 115 through the channels 132. In some implementations, the exterior support 110 can be rigid. In other implementations, the exterior support 110 can be foldable such that the device can be implanted in the eye through a smaller incision than the non-foldable, rigid version.

Figure 24:
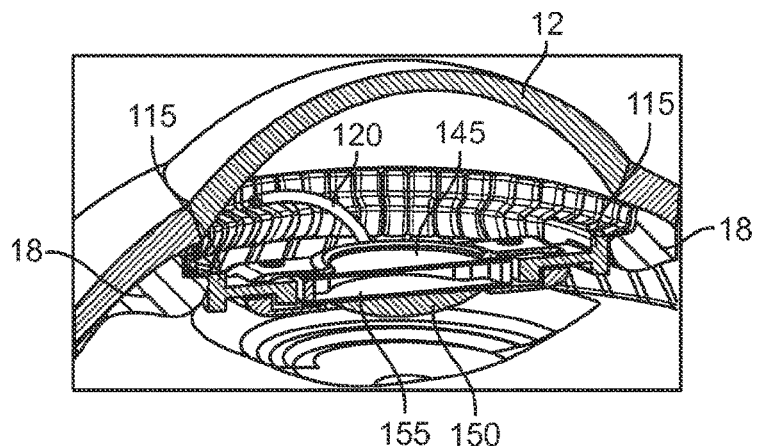
FIG. 24 is a cross-sectional, side view of an accommodating intraocular lens device positioned within the eye shown without the iris such that the haptic is visible.

The exterior support 110 can be bonded or coupled to one or more stabilization haptics 120. In some implementations, the stabilization haptics 120 can be coupled to the exterior support 110 via an element 121 encircling at least a portion of the central annular region 125 of the exterior support 110 (best shown in FIG. 21). In other implementations, the stabilization haptics 120 can be coupled directly to the exterior support 110 without element 121 (see FIG. 24). The stabilization haptics 120 can be static haptics configured to maintain alignment of the optics of the device and to resist movement of the device once implanted and undergoing accommodative shape change. The stabilization haptics 120 can be positioned and engaged within the sulcus 16 and/or the capsular bag to maintain the stability of the device 100 during motion of the force translation arms 115 to prevent and/or limit anterior, posterior, rotational movements of the device. The haptics 120 can include biting elements 160 near their terminal ends having a grooved edge 162 and a hole 164 to improve fixation of the haptic within the eye (see FIG. 2B). The haptics 120 can be any of a variety of haptic designs or combination of haptic designs including, but not limited to open-loop, closed-loop, plate-style, plate loop, monobloc-plate style, j-loop, c-loop, modified J-loop, multi-piece, single-piece, angulated, planar, offset, etc. The haptics 120 can be coaxial or coplanar with the force translation arms 115. The haptics 120 can also be positioned along a different axis than the force translation arms 115, for example, offset from the force translation arms 115 or angulated relative to the force translation arms 115. In some implementations, the haptics 120 can be positioned at an angle in the range of 0-20 degrees or other degree angle relative to the force translation arms 115. Haptics 120 considered herein can include the Rayner designed haptics (Rayner Intraocular Lenses Ltd, East Sussex, UK), NuLens designed haptics (NuLens Ltd., Israel), Staar lens designs (Staar Surgical, Monrovia, Calif.), and others. In some implementations, the haptics 120 can be formed of a biocompatible polymer such as silicone, polyurethane, PMMA, PVDF, PDMS, polyamide, polypropylene, polycarbonate, PEEK, etc. or a combination of such materials. The haptics 120 can be formed of a material or configured to be foldable. In some implementations, the haptics 120 are formed of a shape memory material.

Now with respect to FIGS. 2B, 3A-3F, the lens body 105 can include a shape deformation membrane 140 forming ring-like shape such that it forms a continuous loop or band of material near the periphery of the lens body 105. The shape deformation membrane 140 can have a first end or surface 141, a second end or surface 142, and a sidewall 143 between the first surface 141 and the second surface 142 having an inner surface and an outer surface. The shape deformation membrane 140 can be coupled on the first surface 141 to a shape changing membrane 145, for example on an anterior side of the AIOL 100. The second surface 142 of the shape deformation membrane 140 can be coupled to a static element 150 that does not undergo a shape change, for example on a posterior side of the AIOL 100. The element 150 can be optically clear and provide support function without affecting the optics of the AIOL. The element 150 can also be or include a static lens. It should be appreciated that the anterior membrane can have an anterior support that defines the diameter of the shape changing membrane 145 and is configured to couple the shape deformation membrane to the shape changing membrane 145. The inner surfaces of the shape changing membrane 145, the shape deformation membrane 140 and the static element 150 can collectively form a fixed volume, constant pressure, sealed chamber 155 configured to contain a fixed volume of optical fluid therein. The shape deformation membrane 140, the shape changing membrane 145, and the static element 150 can each include a central portion and deformable portions such that upon coupling together they form the sealed chamber 155 and the central portion 103 and the deformable portions 107 of the lens body 105. The sealed chamber 155 can be a generally planar chamber formed by inner-facing surfaces of the shape changing membrane 145, the static element 150 and the sidewall 143 of the shape deformation membrane 140 and can have a variety of shapes as will be discussed in more detail below.

An outer surface of the sidewall 143 of the shape deformation membrane 140 can be aligned with and bonded to an inner surface of the central region 125 of the exterior support 110 such that the lens body 105 is fixedly positioned within the central region 125. It should be appreciated that the orientation of the lens body 105 within the device 100 and within the eye can vary such that the shape changing membrane 145 can be positioned anteriorly and the static element 150, such as a static lens, positioned posteriorly relative to the eye anatomy. Similarly, the shape changing membrane 145 can be positioned posteriorly and the static element 150 positioned anteriorly relative to the eye anatomy. Further, it should be appreciated that the shape changing membrane 145 and/or the static element 150 can create a sealed chamber 155 within the device 100 by coupling directly to the exterior support 110 rather than the surfaces 141, 142 of the shape deformation membrane 140. Further, the lens can include an anterior support coupled to and defining the diameter of the shape changing membrane 145.

Figure 3A:
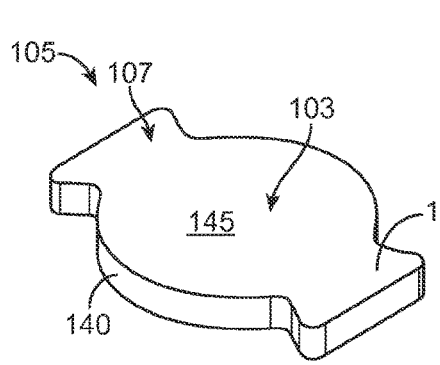
FIG. 3A is a perspective view of a lens body of the AIOL of FIG. 2A.
Figure 3B:
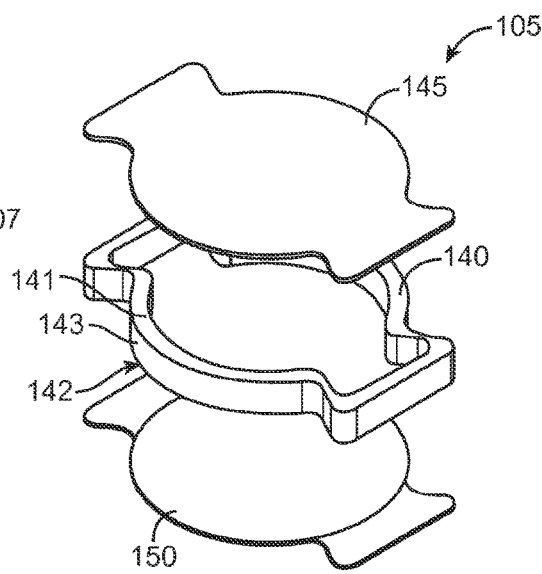
FIG. 3B is an exploded view of the lens body of FIG. 3A.
Figure 3C:
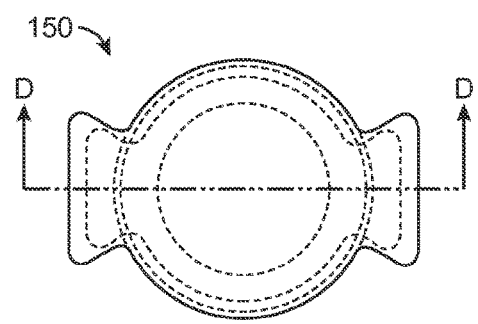
FIG. 3C is a top plan view of a static lens of the lens body of FIG. 3A.
Figure 3D:
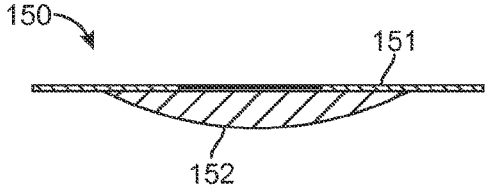
FIG. 3D is a cross-sectional view of the static lens of FIG. 3C taken along line D-D.
Figure 3E:
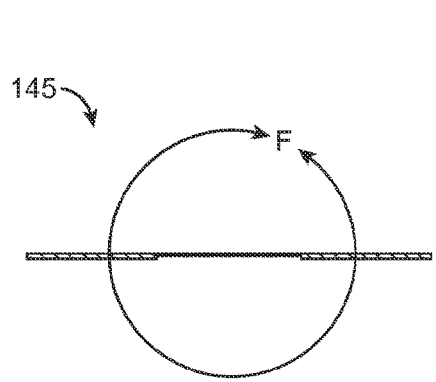
FIG. 3E is a cross-sectional view of a shape changing membrane of the lens body of FIG. 3A.
Figure 3F:
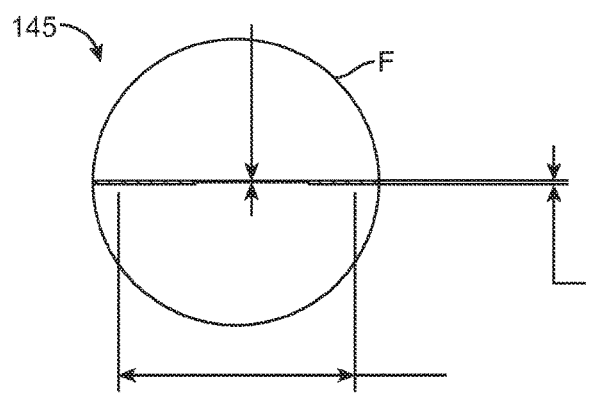
FIG. 3F is a detail cross-sectional view of the shape changing membrane of FIG. 3E of circle F.

FIGS. 3C and 3D illustrate an implementation of the static element 150 having a static lens. The static lens can be formed of silicone, urethane, acrylic material, a low modulus elastomer, or combinations thereof. The static lens can be a static optic to correct to emmetropic state, or can be of an appropriate power for an aphakic patient (usually ±10 D to ±30 D). The static lens can have zero power and form a posterior support to the lens body 105. If the AIOL 100 is being used in conjunction with a separate capsular IOL (e.g. as a "piggyback" lens), the power can be in the range of about −5 D to about +5 D to correct for residual refractive or other optical aberrations in the optical system of the eye. In some implementations, the static lens can have a flat surface 151 and a curved surface 152. The static lens also can be positioned inside the lens body 105 as described above such that the flat surface 151 is in contact with the fluid of the eye and the curved surface 152 forms the inner surface facing the sealed chamber 155 of the lens body 105. In other implementations, the static lens can be positioned outside the lens body 105 such that the flat surface 151 forms the inner surface facing the sealed chamber 155 of the lens body 105 and the curved surface 152 is in contact with the fluid of the eye. The relative refractive indices of the static lens and the fluid surrounding it (whether that is the fluid of the eye or optical fluid within the sealed chamber 155) will determine the shape of the static lens for any given power. The static lens can be plano-convex, convex-plano, convex-convex, concave-convex or any other combination. The static lens can be a spherical lens, aspheric lens, diffractive lens or any combination of both, for example, in order to reduce or compensate for any aberrations associated to the flexible lens.

The shape changing membrane 145 can be a flexible optic formed of an optically clear, low modulus elastomer such as silicone. The shape changing membrane 145 can have a constant thickness such that it is a planar element (see FIG. 4A) or a variable thickness (see FIGS. 3E-3F; and also FIGS. 4B-4E) such that the shape changing membrane 145 has a reduced thickness portion that is relatively more prone to give way, for example upon an increased force applied against an inner surface of the membrane 145 during deformation of the sealed chamber 155. It should be appreciated that the structure of the shape changing membrane 145 can vary. In some implementations, the shape changing membrane 145 can have a linear gradient thickness (FIG. 4B), curved gradient thickness (FIG. 4C), 2, 3 or more thicknesses with a step including radiused or right angles (FIG. 4D), or multiple materials (FIG. 4E), for example materials configured to flex near the accommodating zone (i.e. the region of the membrane 145 undergoing a shape change) and other materials configured to reinforce the optic zone and limit distortion.

In some implementations, the reduced thickness portions of the shape changing membrane 145 can be found near region 170 of the shape changing membrane 145 surrounding, within, or parallel to the optical axis A. The reduced thickness region 170 can be configured to give way due to increased pressure applied by the optical fluid within the sealed chamber 155 on an internal surface of the shape changing membrane 145 causing an outward bowing of the outer face (e.g., anterior face). Region 172 of the shape changing membrane 145 can have a thickness greater than region 170 and can be more resistant to reshaping under such internal pressure applied by the optical fluid in the sealed chamber 155. The regions 172 of the shape changing membrane 145 can continue to provide distance vision correction even when the region 170 is reshaped for near vision. Region 170 of the shape changing membrane 145 can be formed of a material that is relatively more susceptible to outward bowing than the material of region 172. Region 170 can be injection molded in combination with the regions 172 to provide a relatively seamless and uninterrupted outer face. The material of the regions 172 can be generally consistent, though the region 170 can have different stiffness or elasticity that causes it to bow outward farther than the surrounding region. The shape changing membrane 145 can be configured to have varied multifocal capabilities to provide the wearer of the AIOLs described herein with enhanced vision over a wider range of distances, for example, as described in U.S. Publication No. 2009/0234449, which is incorporated by reference herein in its entirety.

Again with respect to FIG. 2H, the shape deformation membrane 140 can include central portion 180 and deformable portions 182. In some implementations, the deformable portions 182 can be coupled to the central portion 180 by a hinge such that the deformable portions 182 are collapsible relative to the central portion 180. The central portion 180 can be aligned with the deformable region 170 of the shape changing membrane 145 (and a central portion of the static element 150) to create the central portion 103 of the lens body 105 that is surrounding, within, or parallel to the optical axis A. The outer surface of the sidewall 143 of the central portion 180 can be aligned with and bonded to an inner surface of the central annular region 125 such that the central portion 103 of the lens body 105 is fixedly attached relative to the central annular region 125 of the exterior support 110. The deformable portions 107 of the lens body 105, in contrast, can be freely moveable within the channels 132 of the side regions 130 of the exterior support 110 such that the deformable portions 107 of the lens body 105 can undergo inward, collapsible movement or displacement relative to the central portion 103 during accommodation as well be described in more detail above.

Figure 2A:
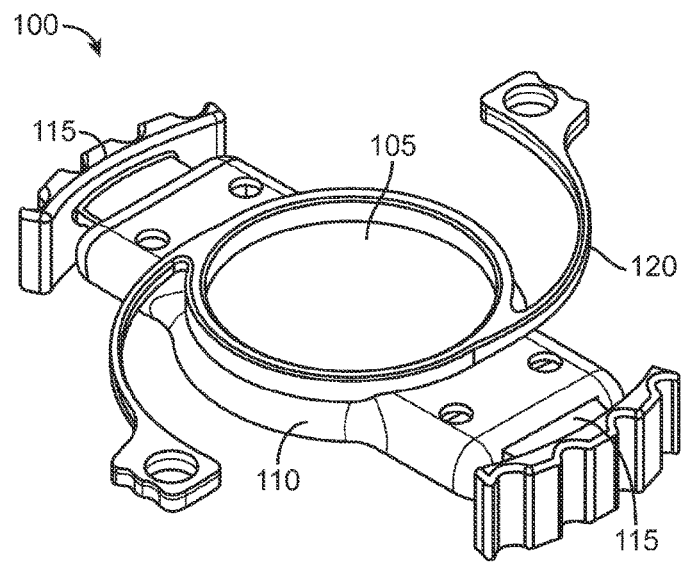
FIG. 2A is a perspective view of an implementation of an accommodating intraocular lens ("AIOL")
Figure 2B:
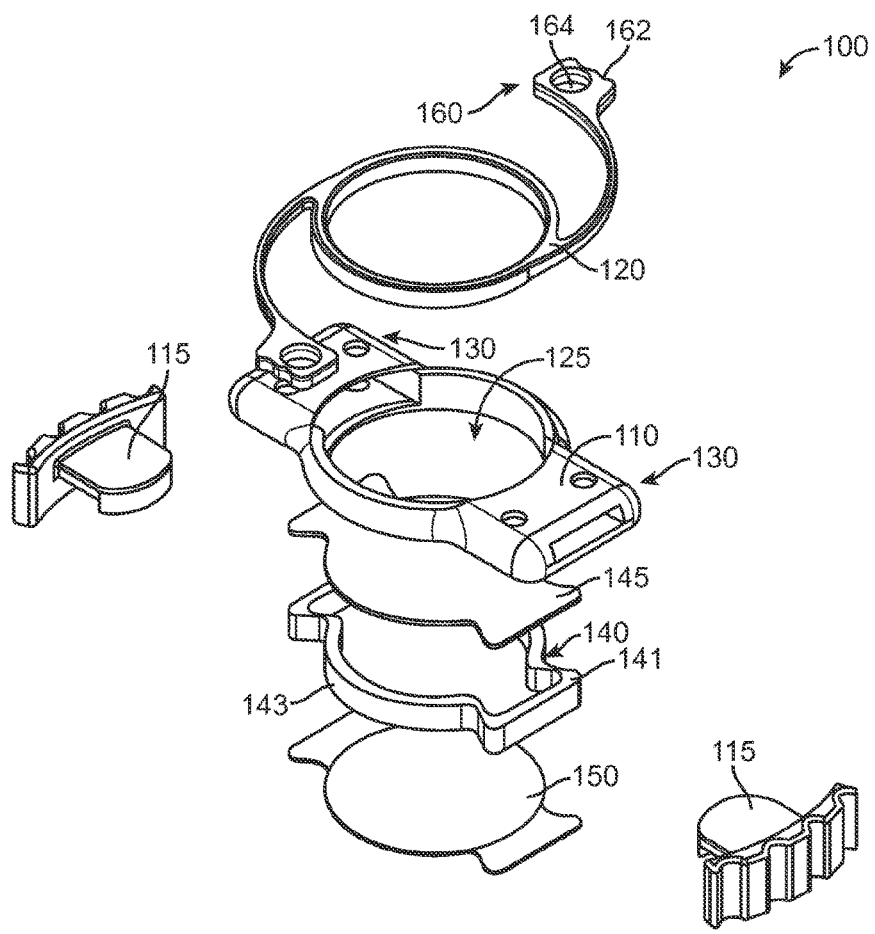
FIG. 2B is an exploded view of the AIOL of FIG. 2A.
Figure 2C:
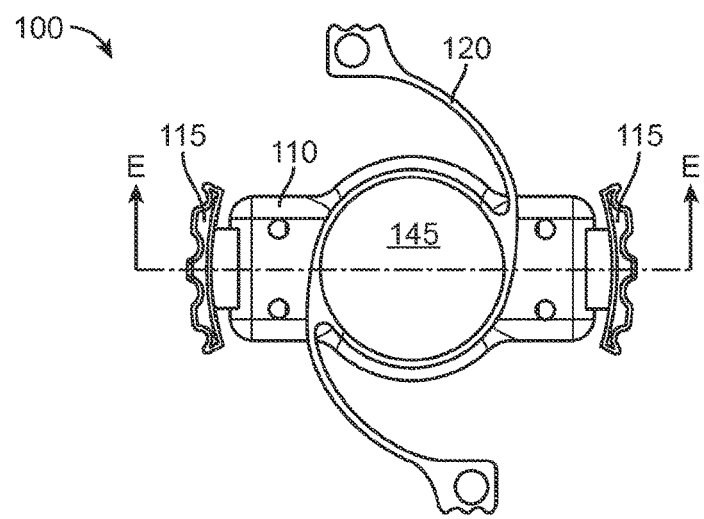
FIG. 2C is a top plan view of the AIOL of FIG. 2A.
Figure 2D:
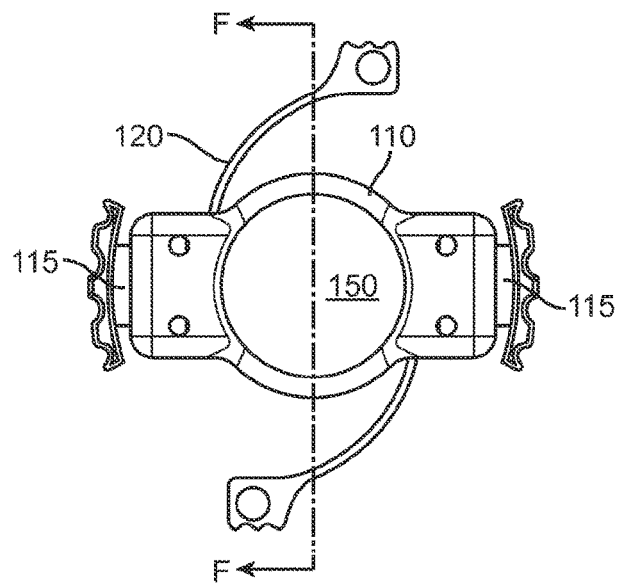
FIG. 2D is a bottom plan view of the AIOL of FIG. 2A.
Figure 2E:
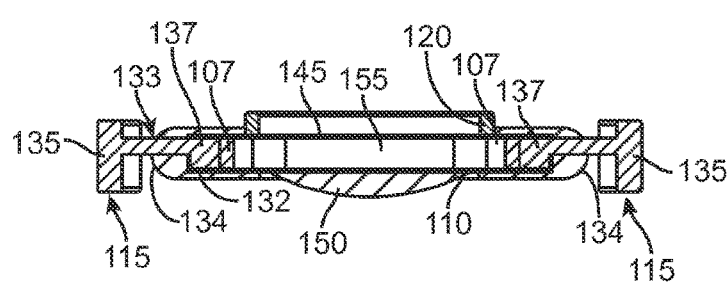
FIG. 2E is a cross-sectional view of the AIOL of FIG. 2C taken along line E-E.
Figure 2F:
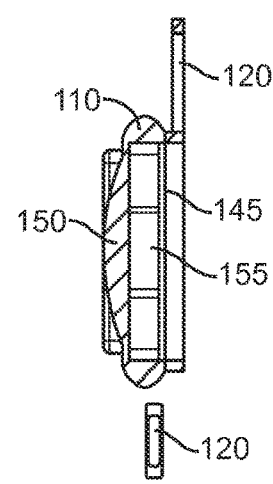
FIG. 2F is a cross-sectional view of the AIOL of FIG. 2D taken along line F-F.
Figure 2G:
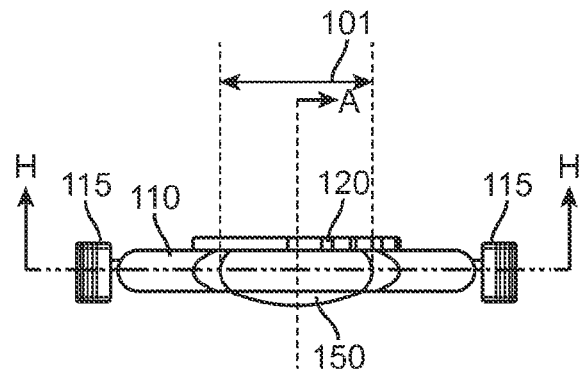
FIG. 2G is a side view of the AIOL of FIG. 2A.
Figure 2H:
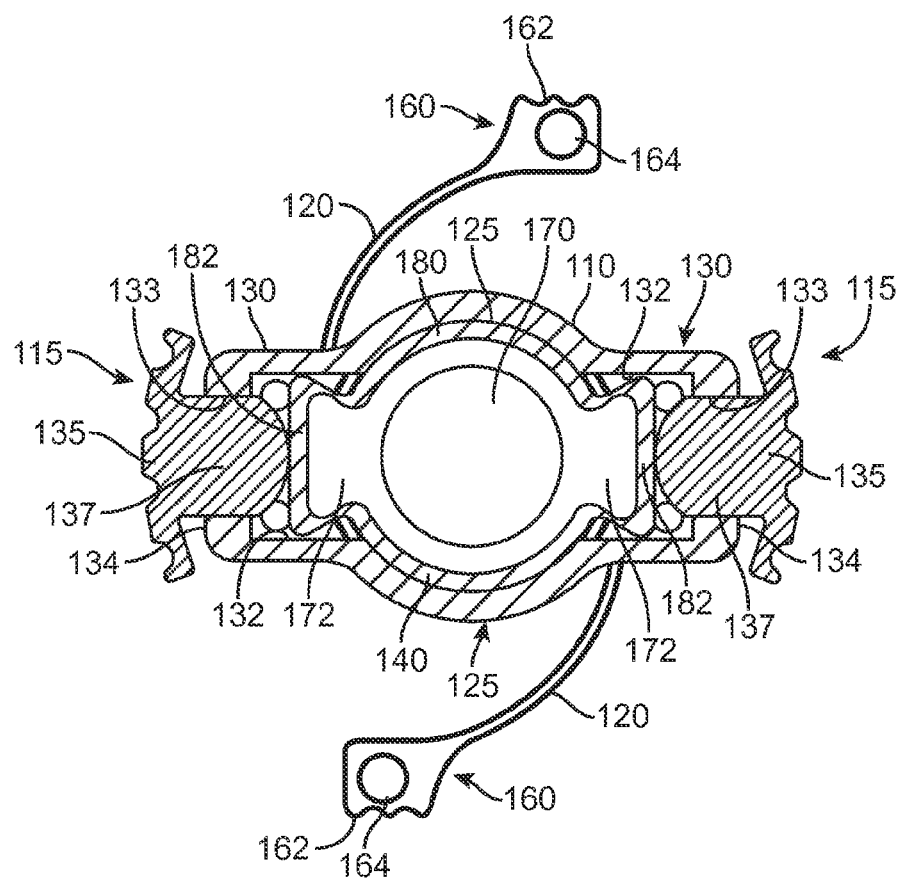
FIG. 2H is a cross-sectional view of the AIOL of FIG. 2G taken along line H-H.

Still with respect to FIG. 2G-2H, the deformable portions 182 are configured to come in contact with contact portion 137 of the force translation arms 115 and be moved relative to the central portion 180. For example, during accommodation the force translation arms 115 can be urged by the one or more ciliary structures towards the optical axis A. Contact portion 135 can be positioned to engage the one or more ciliary structures and contact portion 137 can be positioned against the deformable portion 182 of the shape deformation membrane 140. Contraction can cause the deformable portion 182 of the membrane 140 to undergo movement relative to the central portion 180 of the shape deformation membrane 140. This movement can be a compression, contraction, collapse, indentation, stretch, deformation, hinging or other type of movement that is generally toward the optical axis A. This movement of the deformable portions 182 of the shape deformation membrane 140 (and thus, the deformable portions 107 of the lens body 105) can cause flexure of the shape change membrane 145 in the optic zone 101 without imposing stress or squeezing on the optic zone. The deformable portions 182 can be located inside or outside the optic zone. The optic zone as used herein generally refers to a region of the lens body 105 that surrounds the optical axis and is optically clear for vision. The optic zone is configured to have a corrective power although the entire optic zone may not have the same corrective power. For example, a central region of the optic zone may have corrective power and a peripheral region of the optic zone may not have corrective power.

As mentioned above, the sealed chamber 155 of the lens body 105 can be filed with clear, biocompatible optical fluid. The optical fluid can be a non-compressible liquid or gel that is clear and transparent in the visible spectrum, for example, silicone fluids and gels, functionalized silicone fluids and gels (for example, halogen, i.e., fluorinated silicones, aromatic, i.e., phenyl functionalized silicones, etc.), hydrocarbon and functionalized hydrocarbons, such as long chain hydrocarbons, halogenated hydrocarbons, such as fluorinated and partially fluorinated hydrocarbons, aqueous systems, both fluids and gels, whose refractive index (RI) has been increased by the additions of water-soluble or water swellable polymers, bio-polymer swellable additives such as cellulose, as well as organic or inorganic additives that form nanostructures to increase refractive index. In some implementations, the optical fluid within the sealed chamber 155 has a refractive index higher than 1.37. In other implementations, the optical fluid within the sealed chamber 155 has a refractive index between 1.37-1.57. In other implementations, the optical fluid within the sealed chamber 155 has a refractive index between 1.37-1.60.

The optical fluid within the sealed chamber 155 can cause flexure of the shape changing membrane 145 upon movements of the deformable portions 182 of the shape deformation membrane 140 (and thus, the deformable portions 107 of the lens body 105). Inward movement of the deformable portions 182 can result in the non-compressible optical fluid contained within the fixed-volume sealed chamber 155 of the lens body to press against the surfaces of the sealed chamber 155 including the inner surface of the shape changing membrane 145 and the inner surface of the sidewall 143 of the shape deformation membrane 140. Because the shape changing membrane 145 has a region near the region 170 configured to bow outward upon application of a force, the pressure of the optical fluid against the inner wall of the shape changing membrane 145 results in outward bowing and reshaping of the outer surface of the shape changing membrane 145 upon inward movement of deformable portions 107. The accommodative portion of the optic zone becomes more convex increasing the power of the AIOL 100.

It should be appreciated that this shape change of the shape changing membrane 145 occurs without actual flow of optical fluid from one chamber to another chamber. Rather, a force being applied on the shape deformation membrane 140 to deform the sealed chamber 155 in a first region can cause a reactive deformation of the sealed chamber 155 in at least a second region as the optical fluid inside the sealed chamber 155 changes shape along with the changing shape of the sealed chamber 155. The sealed chamber 155 has a fixed volume, a constant pressure and is deformable. The optical fluid has a fixed volume, is non-compressible, and changes shape depending on the shape of the sealed chamber 155. Inward deformation of one or more portions of the chamber 155 (e.g. the deformable portions 107) can cause a reactive outward deformation of another portion of the chamber 155 (e.g. region 170 of the shape changing membrane 145) due to the non-compressible optical fluid inside the sealed chamber 155. The optical fluid therefore does not actually flow between separate chambers of the AIOL, but rather changes shape alone with the changing shape of the sealed chamber causing the accommodative portion of the optic zone of the shape changing membrane 145 to bow outward increasing the power of the AIOL 100.

Figure 5H:
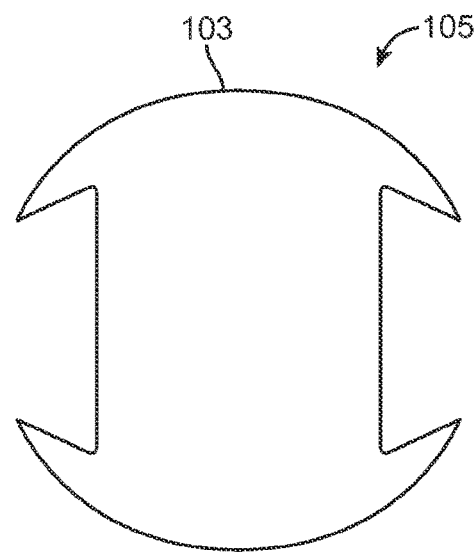
FIG. 5H is a schematic, top plan view of another implementation of a lens body.
Figure 5I:
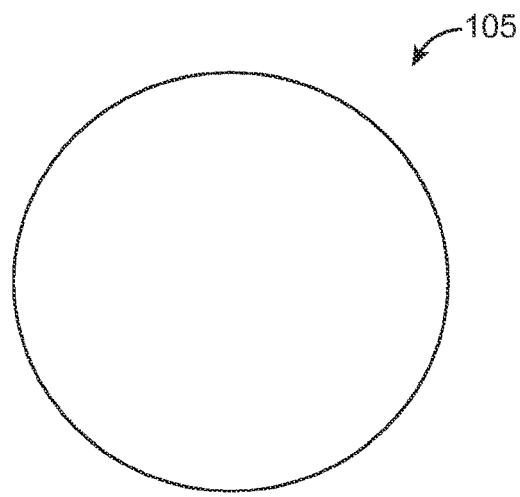
FIG. 5I is a schematic cross-sectional view of an implementation of a lens body and FIG. 5J is a schematic, top plan view of the lens body of FIG. 5I.
Figure 5J:
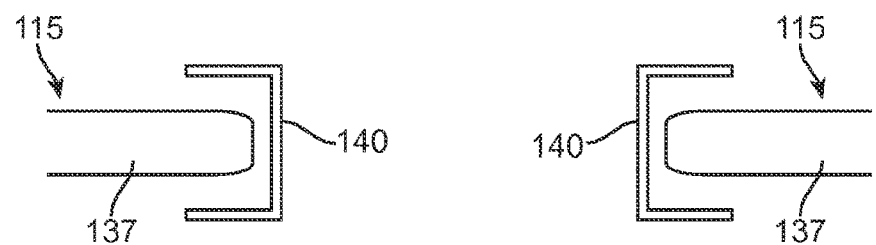

The shape deformation membrane 140, shape change membrane 145, and static element 150 together can form a lens body 105 having any of a variety of shapes. The central portion 103 of the lens body 105 can be generally circular and the deformable portions 107 can have any of a variety of shapes including bellowed, pleated, trapezoidal, cylindrical, elliptical, conical, spherical, hemi-spherical and the like (see for example, FIGS. 5B, 5E, 5G). Further, it should be appreciated that the deformable portions 107 can have any of a variety of cross-sectional shapes along a variety of axes (see for example FIGS. 5A, 5C, 5D, and 5F). The lens body 105 can also be a circular elastomeric ring having a central portion 103 and the deformable region within the optic zone such that the contact portion 137 of the force translation arms 115 contacts the shape deformation membrane 140 within the optic zone as shown in FIGS. 5H, 5I-5J, and also FIG. 25F). The deformable portion 107 of the lens body 105 can be located outside or inside the optic zone (see for example, FIG. 5H), as well as outside or inside the lens body 105. The lens body 105 can have more than two deformable portions 107, including three, four or more deformable portions 107.

The shape deformation membrane 140 can be formed of an optically clear, low modulus elastomer such as silicone, urethane, or flexible inelastic film such as polyethylene. The central portion 180 of the shape deformation membrane 140 can be made of an elastic material. The deformable portions 182 of the shape deformation membrane 140 can be formed of elastic or inelastic materials.

Again with respect to FIGS. 2B and 2H, the devices described herein can include a force translation arm 115 configured to extend through an opening 133 in a sidewall 134 of the side regions 130 of the exterior support 110. As described above, a force translation arm 115 can extend through the opening 133 of one of the side regions 130 and a second force translation arm 115 can extend through the opening 133 of the opposing side region 130. It should be appreciated however that the devices described herein can include less than as well as more than two force translation arms 115. For example, the devices described herein can include one, three, four or more force translation arms 115 arranged evenly around the device. In some implementations, the force translation arms 115 can be a rigid polymer such as silicone, polyurethane, PMMA, PVDF, PDMS, polyamide, polypropylene, polycarbonate, etc., or combinations thereof. In some implementations, the force translation arms 115 can be an element reinforced with PMMA.

In some implementations, the force translation arms 115 can each include an outer, contact portion 135 and an inner, contact portion 137 that can have any of a variety of shapes (see for example FIGS. 2B and 2H). Contact portion 135 can be configured to abut, contact, engage, functionally couple or be in close association with one or more ciliary structures, including but not limited to the ciliary body, ciliary processes, ciliary muscle, the zonules, or a combination thereof to drive shape change of the optics during accommodation and disaccommodation. Contact portion 135 of each force translation arm 115 can remain external to the exterior support 110 such that it can remain in contact with the ciliary structure during accommodation and disaccommodation. In some implementations, the contact portion 135 can have an outer surface having a curved contour that can match a curved contour of a region of the eye in which the contact portion 135 associates. In some implementations, the contact portion 135 can have indentations, grooves, teeth, combs or other surface features to improve, for example, contact and interdigitation with ciliary processes or zonular processes. The outer surface of the contact portion 135 can also have sharpened or beveled edges on an upper and/or lower edge. The contact portions 135 of the force translation arms 115 can incorporate features that improve their connection with the ciliary structures without causing damage. Generally, the contact portions 135 avoid piercing or causing trauma to the ciliary structures. In some implementations, the contact portions 135 can interfere with the ciliary structures such that movement can be transferred without causing trauma to the tissues themselves.

Contact portion 137 can be coupled to contact portion 135. In some implementations, the contact portion 137 can be an elongate element coupled to and extending out from an inner surface of contact portion 135 (see e.g. FIG. 2B). The contact portion 137 can be shaped to be positioned within channel 132 such that at least a portion of the force translation arms 115 can translate within channel 132. Contact portion 137 can abut against at least a region of the lens body 105, such as the deformable portion 182 of the shape deformation membrane 140. For example, as the ciliary muscle 18 contracts during accommodation it constricts towards the optical axis. The ciliary structure can make contact an outer surface of contact portion 135 such that the force translation arms 115 moves within the channel 132 and contact portion 137 presses against the deformable portion 107 of the lens body 105 and causes movement of the deformable portion 107 relative to central portion 103 thereby driving the accommodating shape change of the shape changing membrane 145 as described above.

The position of the force translation arms 115 relative to the one or more ciliary structures can vary. Further, the force translation arms 115 can have a fixed length or can be adjustable. The adjustment of the force translation arms 115 can be performed prior to, during, or any time after insertion in the eye. It should be appreciated that the various components and features described for the various force translation arms can be incorporated with one or more various components and features described with respect to the various devices herein. Any of the devices and systems described herein can incorporate any of a variety of features and components described herein. Components or features of one implementation of a device and system described herein can be incorporated alternatively or in combination with components or features of another implementation of a device and system described herein. For the sake of brevity, explicit descriptions of each of those combinations may be omitted although the various combinations are to be considered herein.

FIG. 6 shows an implementation of a force translation arm 115 having a fixed length. The force translation arm 115 can have an outer contact portion 135 configured to contact one or more ciliary structures, such as the ciliary body. The contact portion 135 can be coupled to an inner contact portion 137 by an elongate element 136. The overall length of the force translation arm 115 can be fixed and an appropriate size selected for each patient based on pre-op measurements.

FIG. 7 shows an implementation of a force translation arm 115 having a length that can be adjusted, for example before, during or any time subsequent to implantation. In this implementation, the force translation arm 115 has a contact portion 135 and a contact portion 137. Contact portion 135 can have a first elongate element 738 extending out from an inner surface of the contact portion 135 and contact portion 137 can have a second elongate element 739 extending out from an outer surface of the contact portion 137. The mechanical adjustment interface between the first elongate element 738 and the second elongate element 739 can be a threaded engagement where an outer surface of a region of the first or second elongate elements 738, 739 can have threads configured to engage corresponding threads on an inner surface of a region of the first or second elongate elements 738, 739. For example, the second elongate element 739 can have threads on an outer surface and be configured to insert into a chamber 731 of the first elongate element 738 to engage with corresponding threads. This threaded engagement between the two portions of the force translation arm 115 allows for on-the-fly adjustments to be made for optimal sizing, for example prior to insertion while the patient is on the table, during or any time after implantation of the device within the eye.

The first and second elongate elements 738, 739 can engage one another according to other various mechanical configurations. For example, FIG. 8A shows another implementation of a force translation arm 115 having a length that can be adjusted. In this implementation, the force translation arm 115 has a contact portion 135 and a contact portion 137. Contact portion 135 can have a first elongate element 738 extending out from an inner surface of the contact portion 135 and contact portion 137 can have a second elongate element 739 extending out from an outer surface of the contact portion 137. The first elongate element 738 and the second elongate element 739 can be aligned adjacent to one another until a desired overall length of the force translation arm 115 is achieved. Alternatively, the first and second elongate elements 738, 739 can be aligned coaxial with one another such that one of the elongate elements inserts through a bore into the chamber 731 of the opposite elongate element (see FIG. 8B). In both configurations, a region of the first and second elongate elements 738, 739 can be mechanically fixed together such as by crimping at a crimp site 861 once the desired length is achieved. This type of adjustment can be performed, for example, prior to, during, or any time after implantation of the device within the eye.

Figure 9:
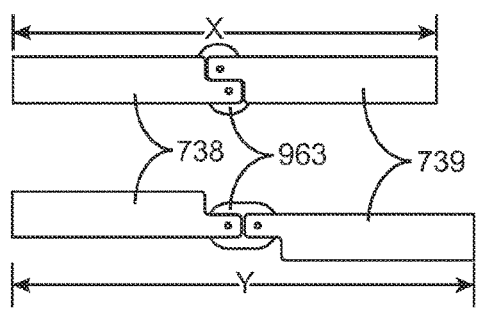
FIG. 9 is a schematic top plan view of an implementation of a force translation arm extending between a ciliary structure and a lens body.

In another interrelated implementation as shown in FIG. 9, once desired length between contact portions 135, 137 is achieved, the first and second elongate elements 738, 739 can be fixed together such as by a sliding cam mechanism 963. The first elongate element 738 can have an irregularly shaped shaft having an end that is configured to contact a corresponding end of the second elongate element 739 also having an irregular shape. As the end of the first elongate element 738 is passed beyond the end of the second elongate element the two irregularly shaped shafts snap into locking engagement with one another.

Figure 10:
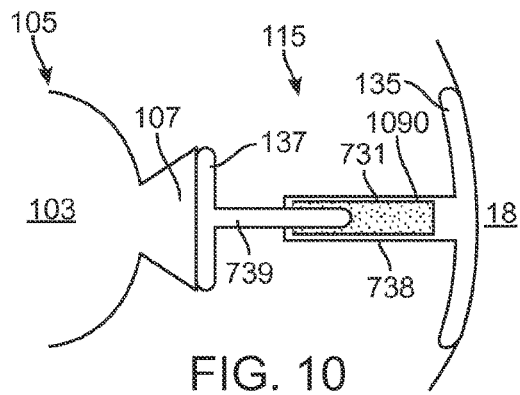
FIG. 10 is a schematic top plan view of an implementation of a force translation arm extending between a ciliary structure and a lens body.

In another interrelated implementation as shown in FIG. 10, the first and second elongate elements 738, 739 can engage one another forming a piston system. The first elongate element 738 can include a chamber 731 and an end of the second elongate element 739 can extend through a bore into the chamber 731. The chamber 731 can be filled to desired volume with an incompressible material 1090 to adjust the effective length of the elements 738, 739 relative to one another. The chamber 731 can be filled during the surgical procedure to fine-tune the effective length of the force translation arms 115.

Figure 11:
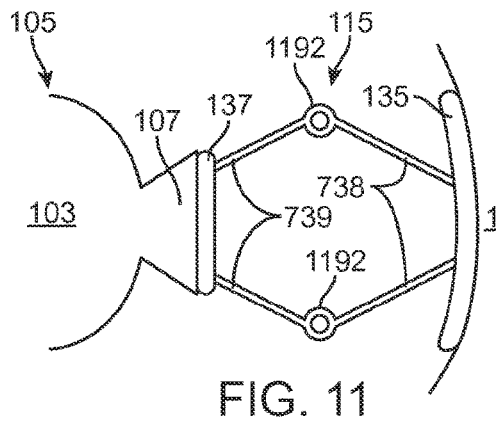
FIG. 11 is a schematic top plan view of an implementation of a force translation arm extending between a ciliary structure and a lens body.

In another interrelated implementation as shown in FIG. 11, contact region 135 can be coupled to contact region 137 by a flexible hinge mechanism 1192. In some implementations, the contact region 135 is coupled to a first elongate element 738 and contact region 137 is coupled to a second elongate element 739. The first elongate element 738 mates with the second elongate element 739 via the hinge mechanism 1192. It should be appreciated that the contact region 135 can have more than one elongate element 738 and contact region 137 can have more than one elongate element 739 that each couple together, respectively, by a hinge mechanisms 1192. The flexible hinge mechanism(s) 1192 can be adjusted prior to or during the procedure. In some implementations, the hinge mechanism 1192 can be fixed in place via thermal/radiation/chemically induced curing. The hinge mechanism 1192 can be configured to rotate in a direction such that the elongate force translation arms 738, 739 fold outward or inward. It should also be appreciated that one or more hinge mechanisms 1192 can fold along one or more axes to provide not only adjustment between the optical axis A and the ciliary structure, but also adjustment in an anterior and/or posterior direction.

Figure 12:
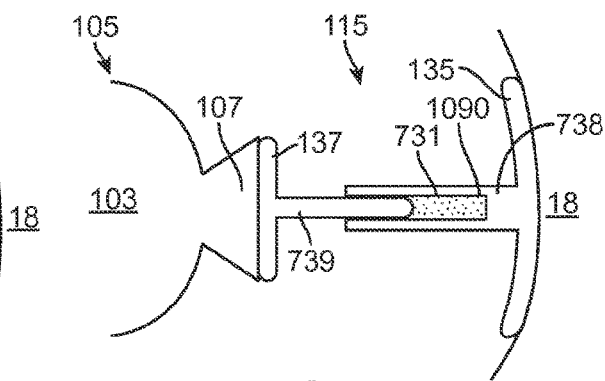
FIG. 12 is a schematic top plan view of an implementation of a force translation arm extending between a ciliary structure and a lens body.

In another interrelated implementation as shown in FIG. 12, the coupling between first and second elongate elements 738, 739 can additionally or alternatively involve a chemical linkage. For example, the first and second elongate elements 738, 739, can be associated and then chemically fixed together using a chemical material such as an adhesive or an activating material such as thermo/radiation cured polymers or other materials. The material can be introduced at the interface between the first and second elongate elements 738, 739. In some implementations, the first elongate element 738 can include a chamber 731 that can be at least partially filled with material 1090 such that the material 1090 surrounds the outer surface of the second elongate element 739 inserted through a bore into the chamber 731. Once a desired length adjustment is achieved, the material 1090 can be activated to fix the interface between the first and second elongate elements 738, 739. The activation can be performed, for example, on the table prior to insertion in the eye or after insertion of the device in the eye such that measurement, adjustment and fixation are performed after implantation of the device 100.

Figure 13:
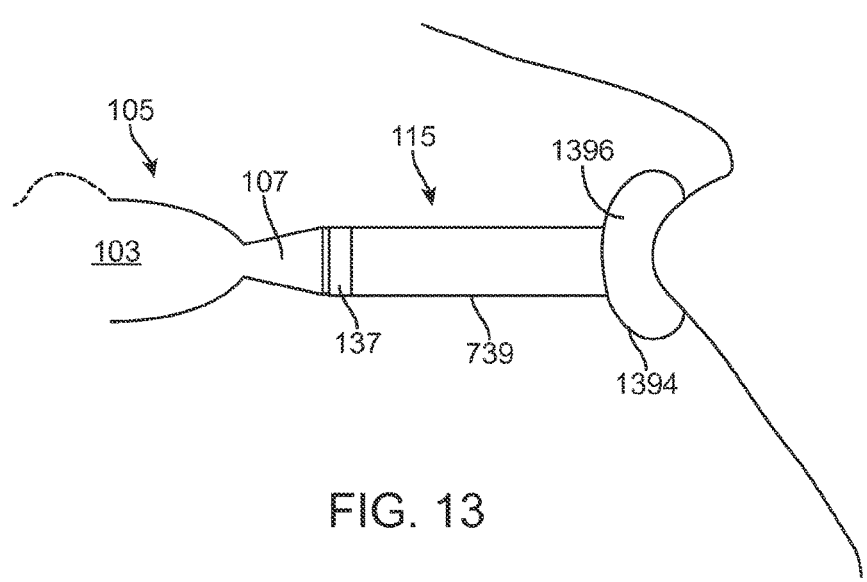
FIG. 13 is a schematic side view of an implementation of a force translation arm extending between a ciliary structure and a lens body.

In an interrelated implementation as shown in FIG. 13, the force translation arm 115 can include contact portion 137 coupled by an elongate element 739 to a contact portion that can be a membrane 1394 having an internal volume 1396 configured to contain a material. The material can include a volume adjustable material that can be locked in situ such as a thermosensitive glue, shape-memory alloys, shape-memory polymers, curable polymer, thermo/radio activated material or other material that allows for on-the-fly adjustment in volume and space.

It should be appreciated that the force translation arms 115 need not move relative to the exterior support 110 and the lens body 105. For example, the force translation arms 115 can be configured to generate an electric current generated upon ciliary structure motion and contact. For example, the force translation arms 115 can incorporate a piezoelectric system that generates an electric charge in response to the mechanical stress applied by the ciliary structures. The current generated by the force translation arms 115 can be used to cause accommodation in the lens body 105. For example, an external surface of contact portion 135 can include a piezoelectric disk that generates a voltage and cause accommodation of the lens.

Figure 14A:
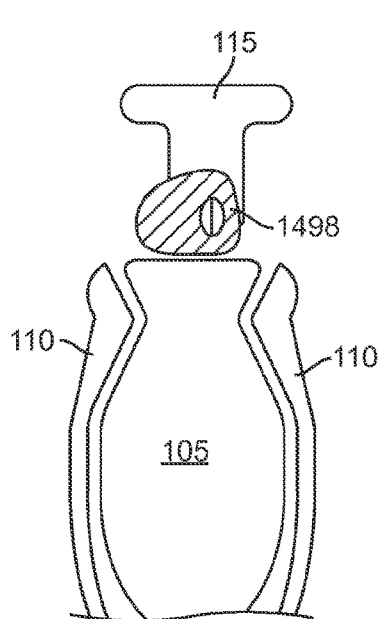
FIGS. 14A-14B are a schematic top plan view of an implementation of a power adjustment mechanism for the devices described herein.
Figure 14B:
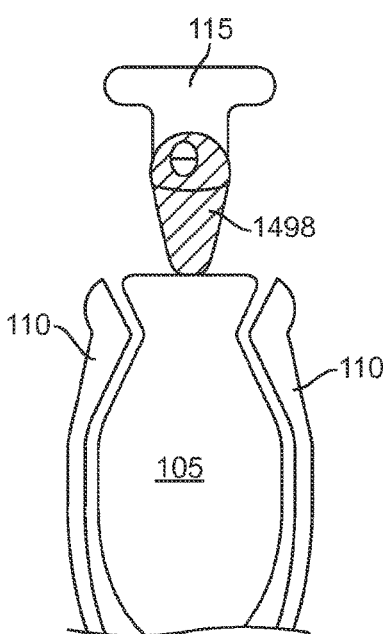

As mentioned herein the overall length of the force translation arms 115 can be adjusted and fine-tuned before, during or after implantation for individual patients, as described above, to achieve customized and optimized contact between the force translation arms 115 and the ciliary structures such that shape change is in turn optimized. It should be appreciated that the shape change achieved in the lens body 105 can also be adjusted and fine-tuned any time after implantation of the device 100. In some implementations and as shown in FIGS. 14A-14B and similar to the implementation shown in FIG. 9, the device 100 can incorporate a cam 1498. The cam 1498 can be positioned between the contact portion 137 of the force translation arm 115 and the deformable portion 107 of the lens body 105 such that they swing about one another. The position of the cam 1498 can be changed such as by rotation by a lever or other element such as a twisting mechanism. The cam 1498 is shown in a first "relaxed" position in FIG. 14A and in a max "active" position in FIG. 14B.

Figure 15:
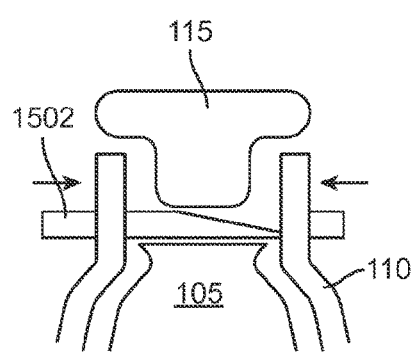
FIG. 15 is a schematic top plan view of an implementation of a power adjustment mechanism for the devices described herein.

In an interrelated implementation as shown in FIG. 15, a rod, shim, spacer, wedge or other adjustment element 1502 can be incorporated to adjust the relative contact between the contact portion 137 of the force translation arm 115 and the deformable portion 107 of the lens body 105. The adjustment element 1502 can be inserted through a corresponding aperture in the exterior support 110 such that the further it is inserted the greater pressure it creates on the deformable portion 107 of the lens body 105 and the greater the shape change. The adjustment element 1502 can be locked into position upon reaching a desired power adjustment. The adjustment element 1502 can also be released such that the power adjustment can be further fine-tuned by withdrawal of the adjustment element 1502 from the exterior support 110. The position of the adjustment element 1502 relative to the exterior support 110 can be adjusted in a variety of on-the-fly amounts depending on the depth of penetration of the adjustment element 1502 towards or away from the exterior support 110. Alternatively, the adjustment element 1502 can have a stepped profile such that it can be "clicked" into position one or two or more pre-set amounts. Further, one or more portions of the adjustment element 1502 can be coated with a thermo-sensitive adhesive for fixation following adjustment.

Figure 16:
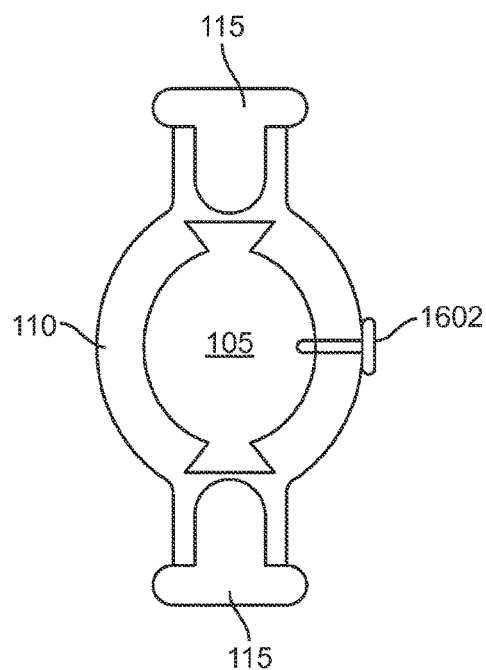
FIG. 16 is a schematic top plan view of an implementation of a power adjustment mechanism for the devices described herein.
Figure 17:
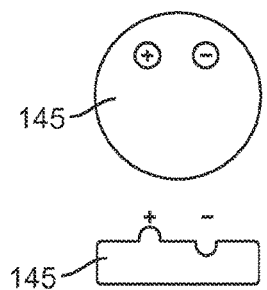
FIG. 17 is a schematic top plan view of an implementation of a power adjustment mechanism for the devices described herein.

In an interrelated implementation as shown in FIGS. 16 and 17, the pressure applied to the lens body 105 can be adjusted separately from that applied by the force translation arms 115 onto the deformable portions 107 of the lens body 105. For example, an adjustable element 1602 such as a screw, lever, or rod can be inserted through the exterior support 110 to make contact with a region of the lens body 105, such as against the shape deformation membrane 140 near the central portion 103 of the lens body. The adjustable element 1602 can apply additional force on the shape deformation membrane 140 such that the optical fluid within the sealed chamber 155 is further urged against the shape changing membrane 145. The adjustable element 1602 can be incrementally adjustable in order to fine-tune the pressure applied such that power adjustment can be achieved. This mechanism can also provide a general solution to power adjustment in the AIOL without accommodation. FIG. 17 illustrates a method of using a material that can be expanded or shrunk in situ in order to change the base power of the lens body 105. In this implementation, rather than inserting a screw or other mechanical feature against the lens body 105, a tension on the shape change membrane 145 (or the static element 150) can be adjusted. For example, the material can be a thermal sensitive material that upon thermal activation can create a bleb. Changes in tension and volume on the lens body can occur depending on whether a bleb, an indentation, or a flattening is formed upon activation of the material.

Figure 18:
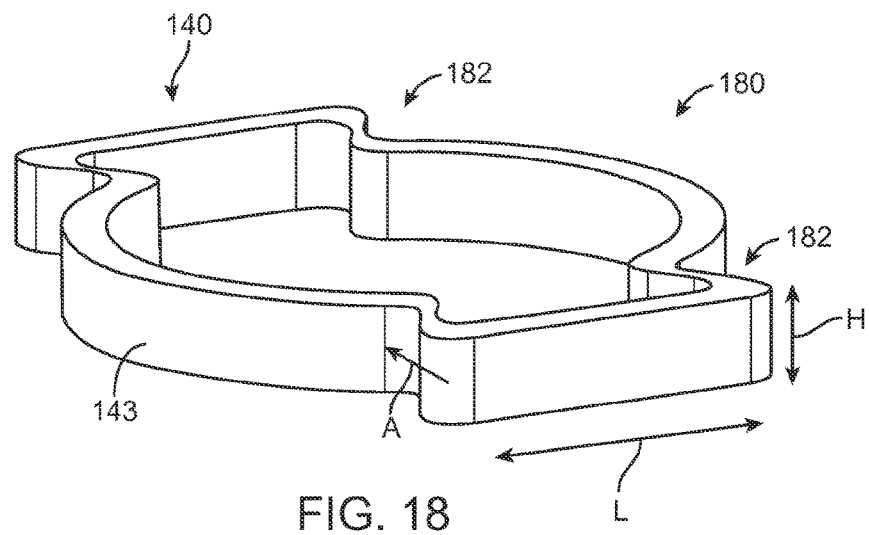
FIG. 18 shows a shape deformation membrane 140 having a deformable portion 182 and a central portion 180.

FIG. 18 shows a shape deformation membrane 140 having two deformable portions 182 and a central portion 180. The deformable portions 182 can be compressible or collapsible or otherwise configured to undergo movement relative to the central portion 180 toward (and also away from) the optical axis A. In this implementation, the deformable portions 182 are generally rectangular shaped and can be displaced or move in response to a force applied from an outer surface of the sidewall 143 of the shape deformation membrane 140 that is in the direction of arrow A without the central portion 180 undergoing a movement or displacement. This displacement of the shape deformation membrane 140 of the closed system can result in the optical fluid contained within the sealed chamber pressing against the inner surface of the shape changing membrane and an outward bowing of a shape changing membrane coupled to the shape changing membrane maintaining pressure within the closed system constant.

Table 1 below illustrates the relationship between the displacement of the deformable portions 182 (displacement from each side) and the outward bowing (and thus, dioptric change or accommodation) of the shape changing membrane that would result. The lens diameter in mm is the region of the shape changing membrane that is configured to bow outwardly in response to the optical fluid pressing against it from within the sealed chamber. The optical fluid can be a silicone oil having a refractive index between 1.37-1.57. The compressible portion length is the length (arrow L) of the deformable portion 182 of the membrane 140 and the compressible portion height (arrow H) is the thickness of the sidewall 143 of the shape deformation membrane 140 (see FIG. 18). Displacement from each compressible portion (i.e. the deformable portion(s) 182 relative to the central portion 180 of the shape deformation membrane 140 or, in terms of the lens body 105, the deformable portion(s) 107 relative to the central portion 103) equals the volume V of the sealed chamber 155 divided by the product of the length L of the compressible portion, the height H of the compressible portion and 2 or V/(L*H*2). The volume of the lens bowing is:

$$V = \frac{\pi h}{6}(3a^2 + h^2),$$

The lens height (h) can be calculated from Pythagoras equation: $(r-h)^2+a^2 \; r^2$. Hence: $h=r-\sqrt{(r^2-a^2)}$.

For example, if the refractive index of the optical fluid is 1.4 and the diameter of the lens is 3 mm, a 28 micron movement from each deformable portion 182 creates a sufficient amount of pressure applied by the optical fluid against the shape changing membrane to form a 1 D lens and if the diameter of the lens is 3 mm, a 84 micron movement of each deformable portion 182 creates a sufficient amount of pressure applied by the optical fluid against the shape changing membrane to form a 3 D lens.

TABLE 1

| Lens Diameter (mm) | Refractive Index of optical fluid | Compressible portion Length (mm) | Compressible portion height (mm) | Displacement (mm) from each side | Diopters (D) |
| --- | --- | --- | --- | --- | --- |
| 3   | 1.4  | 2   | 0.6 | 0.026 | 1 |
| 3.5 | 1.4  | 2   | 0.6 | 0.048 | 1 |
| 4   | 1.4  | 2   | 0.6 | 0.082 | 1 |
| 3   | 1.4  | 2   | 0.6 | 0.052 | 2 |
| 3.5 | 1.4  | 2   | 0.6 | 0.096 | 2 |
| 4   | 1.4  | 2   | 0.6 | 0.164 | 2 |
| 3   | 1.4  | 2   | 0.6 | 0.078 | 3 |
| 3.5 | 1.4  | 2   | 0.6 | 0.144 | 3 |
| 4   | 1.4  | 2   | 0.6 | 0.246 | 3 |
| 3.5 | 1.4  | 2.5 | 0.7 | 0.099 | 3 |
| 4   | 1.57 | 1.8 | 0.5 | 0.089 | 3 |

Figure 19:
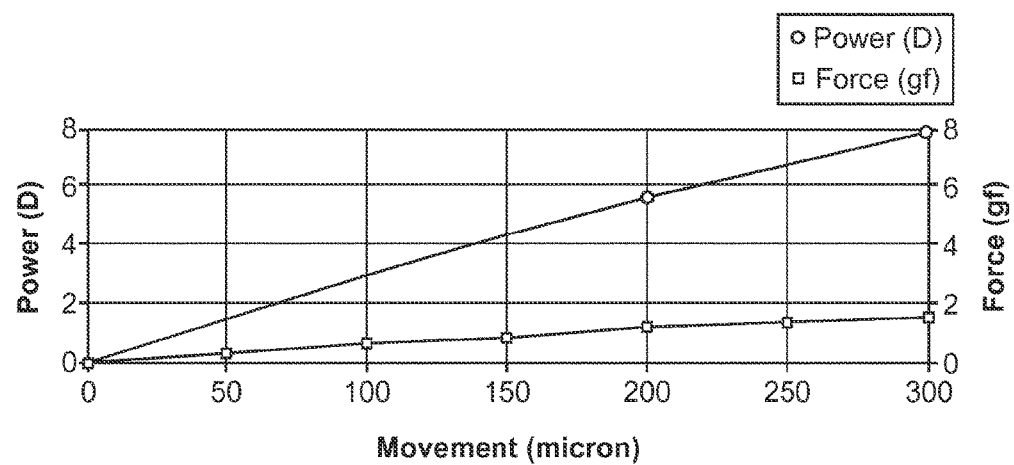
FIG. 19 illustrates the optical power (D) achieved in a lens body upon movement (um) of a shape deformation membrane upon application of a force (go.

FIG. 19 illustrates the optical power (D) achieved in a lens body upon movement (um) of a shape changing membrane upon application of a force (gf). The devices described herein were evaluated using an optical bench test for the evaluation of intraocular lenses (IOLA PLUS, Rotlex, Israel) and calibrated load cell (Advanced Force Torque Indicator (AFTI), Mecmesin, UK) and were shown to achieve about 3 D change upon 100 um movement and application of 1 gf.

Figure 20:
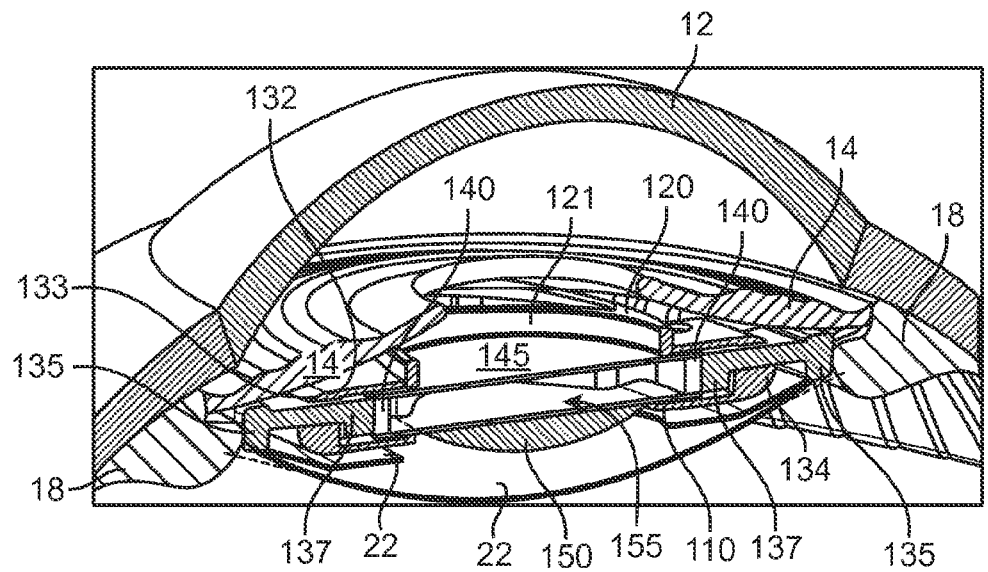
FIG. 20 is a cross-sectional, partial perspective view of an accommodating intraocular lens device positioned within the eye.
Figure 21:
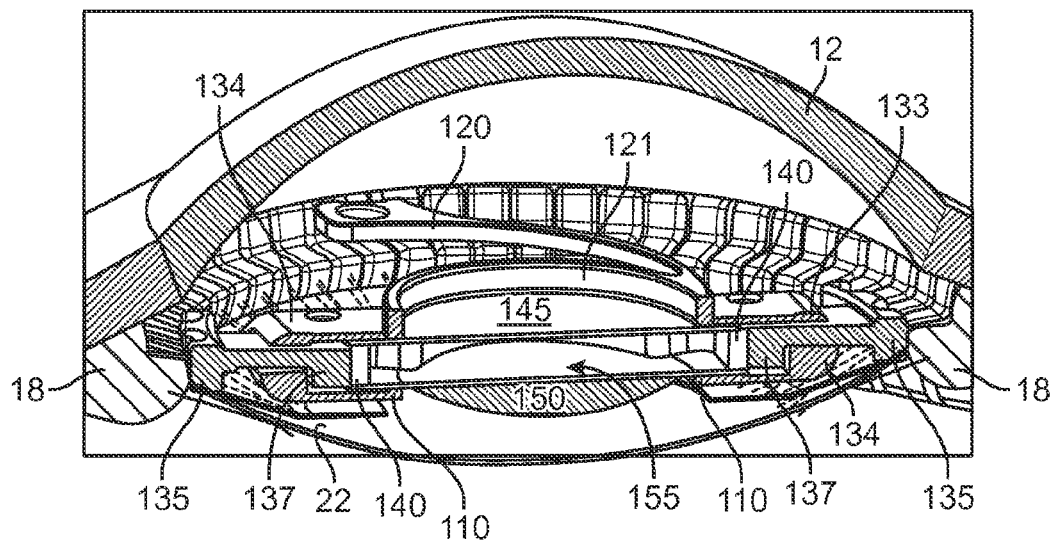
FIG. 21 is a cross-sectional perspective view of the device of FIG. 20 positioned within the eye shown without the iris such that the haptic is visible.
Figure 22:
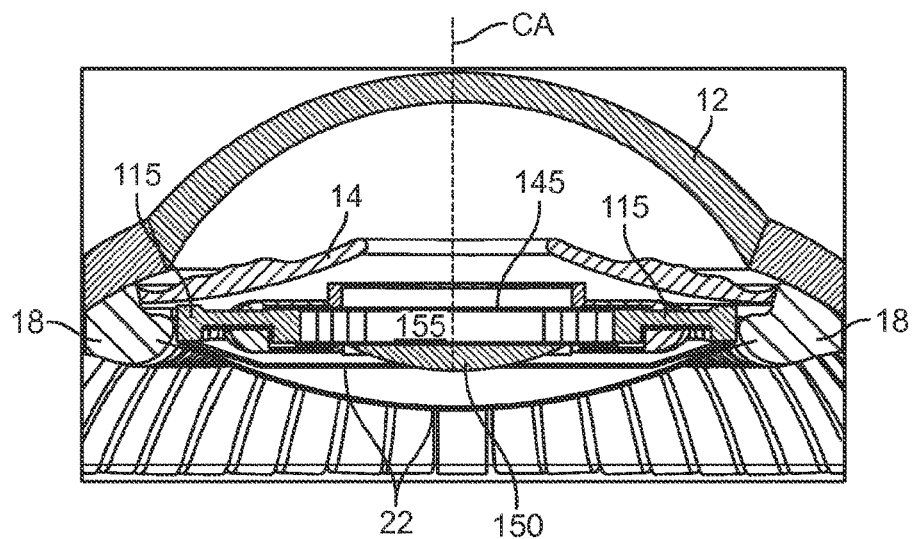
FIG. 22 is a cross-sectional, side view of the device of FIG. 20 in an unaccommodated state.
Figure 23:
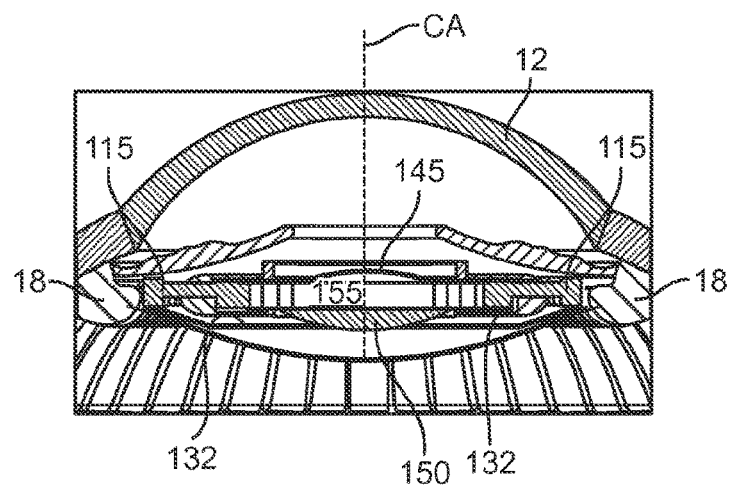
FIG. 23 is a cross-sectional, side view of the device of FIG. 20 in an accommodated state.

FIG. 20 shows a cross-sectional, partial perspective view of an AIOL 100 positioned within an eye and FIG. 21 is a cross-sectional perspective view of the AIOL 100 positioned within the eye shown without the iris such that the haptic 120 is visible. FIG. 22 is a cross-sectional, side view of the AIOL 100 positioned in the eye and in an unaccommodated state. FIG. 23 is a cross-sectional, side view of the AIOL 100 positioned in the eye and in an accommodated state. As with the various implementations described throughout, the AIOL 100 can include a lens body 105 having a sealed chamber 155 formed of the inner surfaces of the shape deformation membrane 140, the shape changing membrane 145 and the static element 150 and configured to contain optical fluid therein. The lens body 105 can be positioned within and coupled to a support 110. The AIOL 100 can include a force translation arm 115 and a stabilization haptic 120. The stabilization haptic 120 can be positioned posterior to the iris 14 within the sulcus 16 (see FIG. 24) such that the AIOL 100 is stabilized and fixed by the interaction of the haptic 120 within the sulcus 16. The AIOL 100 can also be implanted such that the stabilization haptic 120 is positioned within the capsular bag. An anterior surface of the central portion of the shape changing membrane 145 can be aligned within a central annular region 125 of the support 110 and can be configured to bow outwardly upon contraction of the ciliary muscle 18, i.e. during accommodation. The AIOL 100 is shown implanted within an eye having undergone capsularhexis of the capsular bag 22 such that the static element 150 is positioned on a posterior-most side of the device 105 and remains generally external to the capsular-hexis (see FIG. 20). The static element 150 can be a static lens powered for distance as described herein.

The devices described herein can be actuated into an accommodated (or unaccommodated) shape in direct response to ciliary structure movements, for example movements of the ciliary body and/or ciliary muscle. This direct ciliary translation of accommodation of the devices described herein can involve movement of optical fluid within the sealed chamber. As described above, and as shown also in FIGS. 20-23, the force translation arms 115 can directly contact one or more ciliary structures to cause actuation of the force translation arms 115 such that the contact portion 137 can be positioned within the channel 132 in a first configuration in which the force translation arm 115 is generally positioned away from a central axis CA of the device 105 (see FIG. 22) to a second configuration in which the force translation arm 115 is urged by the ciliary structure towards the central axis CA of the device 105 (see FIG. 23). The shape changing membrane 145 can be generally planar when the force translation arms 115 are in the first configuration (i.e. unaccommodated) and the shape changing membrane 145 can be bowed outwardly when the force translation arms 115 are in the second configuration (i.e. accommodated). This can be due to the contact portion 137 of the force translation arms 115 pressing against shape deformation membrane 140 such that the deformable portion 107 of the lens body collapses or moves inward towards the central portion 103 of the lens body 105. The collapse of the deformable portion 107 can cause optical fluid within the sealed chamber 155 to press against the internal surfaces of the chamber 155 until the anterior surface of the shape changing membrane 145 takes on a more spherical or convex shape such as due to an outward bowing along the optical axis (see FIG. 23).

FIGS. 25A-25G illustrate an interrelated implementation of an accommodating intraocular lens ("AIOL") 200 according to the descriptions provided herein. It should be appreciated that the features and components of the devices described herein can be interrelated and used in combination or in the alternative. For the sake of brevity some of the descriptions regarding the components of the various implementations of devices described herein are not reiterated although it should not be construed to mean those previous descriptions do not apply to the following implementations.

The AIOL 200 can include a lens body 205, a support 210, force translation arms 215, and one or more stabilization haptics 220. The support 210 can include an internal and/or external support 210. In some implementations, the support 210 is an external support 210 having a central annular region with which a central portion of the lens body 205 is aligned. The support 210 can include channels 232 or slots through a peripheral sidewall that extend into the central annular region (best shown in FIG. 25F). A force translation arm 215 can extend through a channel 232 on one side of the support 210 and a second force translation arm 215 can extend through a channel 232 on an opposing side of the support 210. The force translation arms 215 can each include an outer, contact portion 235 configured to contact at least a portion of a ciliary structure and an inner, contact portion 237 configured to contact at least a portion of the lens body 205. Contact portion 235 of each force translation arm 215 can remain external to the support 210 such that it can remain in contact with the ciliary structure during accommodation and disaccommodation. Contact portion 237 of each force translation arm 215 can translate within channel 232. The force translation arms 215 can move freely back and forth within channel 232 as the ciliary structure moves to effect accommodative shape change of the lens body 205 as will be described in more detail below.

As with previous implementations, the support 210 can be formed of a rigid polymer, including but not limited to silicone, polyurethane, PMMA, PVDF, PDMS, polyamide, polypropylene, polycarbonate, etc, or combinations thereof. The support 210 can be configured to prevent distortion caused by movement of the force translation arms 215 through the channels 232. The support 210 can be an exterior support located outside the sealed capsule 255 as shown in FIGS. 25A-25G or the support 210 can be located inside the sealed capsule 255 as shown in FIGS. 26A-26F and 27A-27D, which will be described in more detail below. In some implementations, one or more stabilization haptics 220 can be bonded to the exterior support 210. In other implementations, the one or more stabilization haptics 220 can be bonded to a portion of the lens body 205 and the support 210 be located within the sealed chamber of the lens body 205. In other implementations, the one or more stabilization haptics 220 can be molded as part of the lens body 205 or the exterior support 210. The stabilization haptics 220 can be static haptics configured to maintain alignment of the optics of the device and to resist movement of the device once implanted and undergoing accommodative shape change as described in more detail above. In some implementations, the haptic(s) 220 can be placed in the ciliary sulcus or the capsular bag.

The lens body 205 can include a shape deformation membrane 240, a shape changing membrane 245 and a static element 250, which can include a static lens. The shape deformation membrane 240, the shape changing membrane 245 and the static element 250 in combination with the support 210 create a generally planar, sealed chamber 255 that is configured to contain optical fluid therein. The shape deformation membrane 240 can be a ring-shape membrane coupled to an inner surface of the similarly ring-shaped support 210. A region of the shape changing membrane 245 can be coupled to a first surface of the support 210 and a region of the static element 250 can be coupled to a second, opposite surface of the support 210. It should be appreciated that the orientation of the lens body 205 within the AIOL 200 and within the eye can vary such that the shape changing membrane 245 can be positioned anteriorly and the static element 250 positioned posteriorly relative to the eye anatomy. Similarly, the shape changing membrane 245 can be positioned posteriorly and the static element 250 positioned anteriorly relative to the eye anatomy.

The static element 250 is best shown in FIGS. 25B and 25C can be or include a static lens formed of silicone, urethane, or a low modulus elastomer as described above in other embodiments. The shape changing membrane 245 can be a flexible optic formed of an optically clear low modulus elastomer such as silicone. The shape changing membrane 245 can have a constant thickness such that it is a planar element or a variable thickness such that the shape changing membrane 245 has a reduced thickness portion that is relatively more prone to give way due to increased internal pressure as described in more detail above. It should be appreciated that the structure of the shape changing membrane 245 can vary as described herein. The reduced thickness portion can be configured to give way due to increased internal pressure applied by the optical fluid within the sealed chamber 255 causing an outward bowing of the outer face (e.g., anterior face).

Figure 25E:
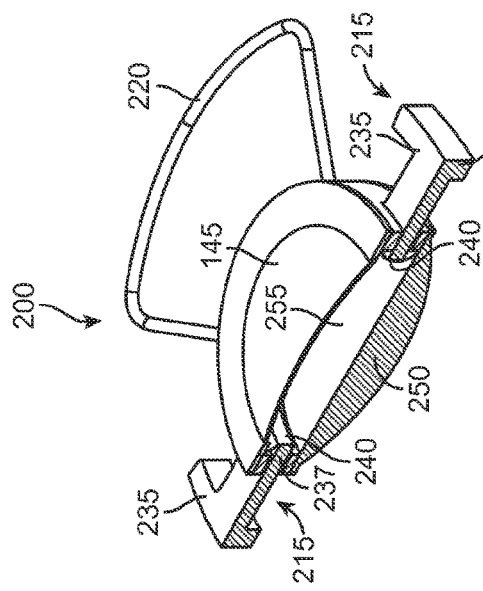
FIGS. 25D and 25E are cross-sectional partial view of the lens of FIG. 25A in a disaccommodated, relaxed state and an accommodated, actuated state, respectfully.
Figure 25G:
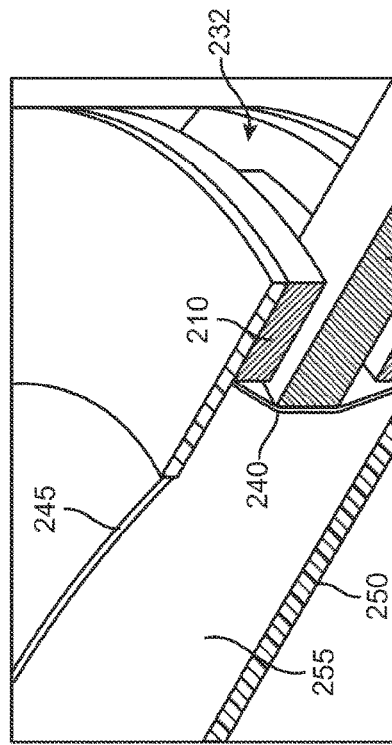
FIG. 25G is a detailed view of FIG. 25E.
Figure 25D:
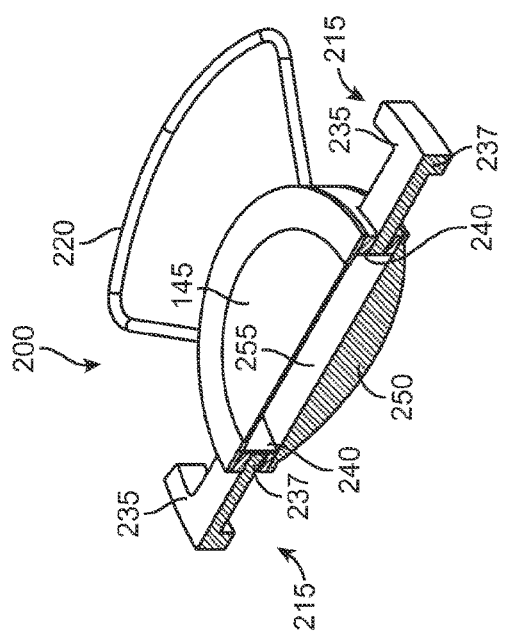
Figure 25F:
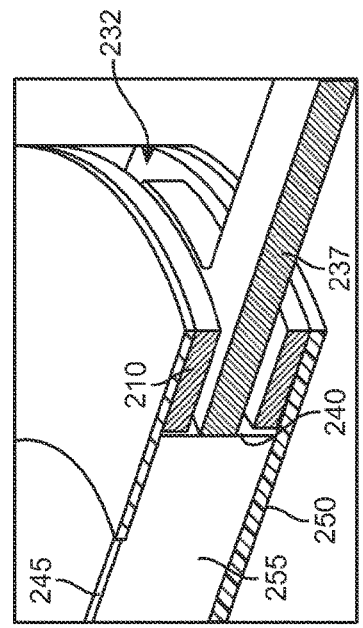
FIG. 25F is a detailed view of FIG. 25D.

Now with respect to FIGS. 25F and 25G, the support 210 can include channels 232 through which the shape deformation membrane 240 can be accessed by the contact portions 237 of the force translation arms 215. For example, during accommodation the force translation arms 215 can be urged by the one or more ciliary structures towards the optical axis A. Inward/anterior movement of the ciliary structure can be harnessed by contact portions 235 causing the force translation arms 215 to move inward through channels 232 toward the optical axis A. Contact portions 237 of the force translation arms 215 can contact the shape deformation membrane 240 and cause the shape deformation membrane 240 to undergo movement relative to the shape changing membrane 245. This movement can be a compression, indentation, stretch, deformation, or other type of movement that is generally toward the optical axis A. This movement of the shape deformation membrane 240 can cause flexure of the shape change membrane 245 into a more spherical or convex shape in the optic zone 201 thereby increasing the power of the lens for near vision focus without imposing stress or squeezing on the optic zone as will be described in more detail below.

As mentioned above, the sealed chamber 255 of the lens body 205 can be filled with optical fluid that can be a clear, biocompatible optical fluid. The optical fluid can be a non-compressible liquid or gel that is clear and transparent in the visible spectrum, for example, silicone fluids and gels, functionalized silicone fluids and gels (for example, halogen, i.e., fluorinated silicones, aromatic, i.e., phenyl functionalized silicones, etc.), hydrocarbon and functionalized hydrocarbons, such as long chain hydrocarbons, halogenated hydrocarbons, such as fluorinated and partially fluorinated hydrocarbons, aqueous systems, both fluids and gels, whose refractive index (RI) has been increased by the additions of water-soluble or water swellable polymers, bio-polymer swellable additives such as cellulose, as well as organic or inorganic additives that form nanostructures to increase refractive index. In some implementations, the optical fluid within the sealed chamber 255 has a refractive index higher than 1.37. In other implementations, the optical fluid within the sealed chamber 255 has a refractive index between 1.37-1.57. In other implementations, the optical fluid within the sealed chamber 255 has a refractive index between 1.37-1.60.

The optical fluid within the sealed chamber 255 can cause flexure of the shape changing membrane 245 upon movements of the shape deformation membrane 240. Inward movement of the shape deformation membrane 240 can result in the non-compressible optical fluid contained within the fixed volume, sealed chamber 255 to press against the surfaces of the sealed chamber 255 including the inner surface of the shape changing membrane 245. Because the shape changing membrane 245 has a region near the central portion configured to bow outward upon application of a force, the pressure of the optical fluid against the inner wall of the shape changing membrane 245 results in outward bowing and reshaping of the outer surface of the shape changing membrane 245. FIGS. 25D and 25E are cross-sectional, partial views of a device in a relaxed, disaccommodated (unaccommodated) state and an actuated, accommodated state, respectfully. The optic zone portion surrounding, within or parallel to the optical axis A becomes more convex increasing the power of the AIOL 200. It should be appreciated that this shape change of the shape changing membrane 245 can occur without actual flow of fluid from one part of the lens body 205 to another as described herein. Rather, the compression of one region of the sealed chamber 255 having a fixed volume filled with a corresponding fixed volume of non-compressible optical fluid drives a reactive shape change of another region of the sealed chamber 255 formed by the shape changing membrane 245.

The AIOL 200 can include force translation arms 215 configured to extend through channels 232 in the support 210. As described above, a force translation arm 215 can extend through the channel 232 of one side and a second force translation arm 215 can extend through the channel 232 of the opposing side. It should be appreciated however that the devices described herein can include more than two force translation arms 215. For example, the devices described herein can include three, four or more force translation arms 215 arranged evenly around the device. In some implementations, the force translation arms 215 can be a rigid polymer such as silicone, polyurethane, PMMA, PVDF, PDMS, polyamide, polypropylene, polycarbonate, etc. or combinations thereof. For example, the force translation arms 215 can be an element of a first material reinforced with a second material, such as PMMA.

In some implementations, the force translation arms 215 can each include an outer, contact portion 235 and an inner, contact portion 237 that can have any of a variety of shapes as described herein. Contact portion 235 can be configured to abut, contact, engage, functionally couple or be in close association with one or more ciliary structures, including but not limited to the ciliary body, ciliary processes, ciliary muscle, the zonules, or a combination thereof to drive shape change of the optics during accommodation and disaccommodation. Contact portion 235 of each force translation arm 215 can remain external to the support 210 such that it can remain in contact with the ciliary structure during accommodation and disaccommodation. In some implementations, the contact portion 235 can have an outer surface having a curved contour that can match a curved contour of a region of the eye in which the contact portion 235 associates. In some implementations, the contact portion 235 can have indentations, grooves, teeth, combs or other surface features to improve, for example, contact and interdigitation with ciliary processes or zonular processes. The outer surface of the contact portion 235 can also have sharpened or beveled edges on an upper and/or lower edge.

Contact portion 237 can be coupled to contact portion 235. In some implementations, the contact portion 237 can be an elongate element coupled to and/or extending out from an inner surface of contact portion 235 (see e.g. FIGS. 25D and 25E). The contact portion 237 can be shaped to be positioned within channel 232 such that at least a portion of the force translation arms 215 can translate within channel 232. Contact portion 237 can abut against the shape deformation membrane 240 as described above. For example, as the ciliary muscle 18 contracts during accommodation it constricts towards the optical axis A. The ciliary structure can make contact an outer surface of contact portion 235 such that the force translation arms 215 moves within the channel 232 and contact portion 237 presses against the shape deformation membrane 240 of the lens body 205 and causes movement of the shape deformation membrane 240 relative to the shape changing membrane 245 thereby driving the accommodating shape change of the shape changing membrane 245 as described above. The shape deformation membrane 240 can be located inside or outside the optic zone of the lens body.

FIGS. 26A-26F illustrate an interrelated implementation of an accommodating intraocular lens ("AIOL") 300 having an internal support 312 that will be described in more detail below. It should be appreciated that the features and components of the devices described herein can be interrelated and used in combination or in the alternative. For the sake of brevity some of the descriptions regarding the components of the various implementations of devices described herein are not reiterated although it should not be construed to mean those previous descriptions do not apply to the following implementations.

The AIOL 300 can include a lens body 305, a support 310, and force translation arms 315. The support 310 can include an internal and/or an external support 310. In some implementations, the AIOL 300 has only an internal support sufficient to support the lens without any additional exterior support. The lens body 305 can be positioned within and coupled to a central region of the support 310. An anterior surface of the lens body 305 can be exposed through an anterior opening of the support 310 and a posterior surface of the lens body 305 can be exposed through a posterior opening of the support 310. It should be appreciated that orientation of the components of the lens body 305 within the AIOL 300 and within the eye can vary and that use of the terms "anterior" and "posterior" are not intended to be limiting.

The support 310 can include channels 332 or slots in a sidewall through which the force translation arms 315 can extend. The force translation arms 315 can move freely back and forth within the channels 332 as the ciliary structures move to effect accommodative shape change of the lens body 305. For example, a first force translation arm 315 can extend through a first channel 332 on one side of the support 310 and a second force translation arm 315 can extend through a second channel 332 on an opposing side of the support 310. The force translation arms 315 can each include an outer, contact portion 335 configured to contact at least a portion of a ciliary structure and an inner, contact portion 337 configured to translated within channel 332 and make contact with the lens body 305. The contact portion 335 of each force translation arm 315 can remain external to the support 310 such that it can remain in contact with the ciliary structure during accommodation and disaccommodation.

The support 310 can be formed of a material configured to prevent distortion caused by movement of the force translation arms 315 as well as prevent inadvertent movements of the force translation arms 315 (e.g. perpendicular to the direction of the force translation arm 315 inward/outward movement). In some implementations, one or more stabilization haptics 320 can be bonded to the support 310. In other implementations, the one or more stabilization haptics 320 can be bonded to a portion of the lens body 305 and the support 310 be located within the sealed chamber of the lens body 305. In other implementations, the one or more stabilization haptics 320 can be molded as part of the lens body 305 or the exterior support 310. The stabilization haptics 320 can be static haptics configured to maintain alignment of the optics of the device and to resist movement (e.g. vertical movement) of the AIOL 300 once implanted and undergoing accommodative shape change as described in more detail above. In some implementations, the one or more haptic(s) 320 can be placed in the ciliary sulcus and/or the capsular bag.

The lens body 305 can include a shape deformation membrane 340, a shape changing membrane 345 or anterior lens element 345, and a static element 350 (or static lens) sealed together into a generally planar lens body 305 having a sealed chamber 355. The sealed chamber 355 is configured to contain optical fluid therein, for example a fluorosilicone oil or other optical fluid described herein. The shape deformation membrane 340 can be a ring-shaped silicone structure (e.g. PDMS) coupled on a first surface (e.g. anterior surface) to a perimeter of the shape changing membrane 345 or an anterior support defining a diameter of the shape changing membrane 345. The shape deformation membrane 340 can be coupled on an opposite surface (e.g. posterior surface) to a perimeter of the static element 350. It should be appreciated that the components of the lens body can be coupled in any of a variety of configurations between themselves as well as with the support 310. The outer wall of the shape deformation membrane 340 can have regions configured to engage with the force translation arms 315 such that as the force translation arms 315 move, the regions likewise move. Movement of the shape deformation membrane 340 changes the shape of the sealed chamber 355 causing accommodation and disaccommodation as will be described in more detail below. In some implementations, the shape deformation membrane 340 can have a first region on the outer wall that engages with a first force translation arm 315 and a second region on the outer wall that engages with a second force translation arm 315. Each of the first and second regions on the outer wall of the shape deformation membrane 340 can include a surface feature 341 configured to engage with a corresponding feature 338 on the force translation arm 315 (best shown in FIG. 26C).

The support 310 can be formed of a harder material (or materials) than the shape deformation membrane 340 to prevent inadvertent movements of the moving parts of the device. The AIOL 300 can alternatively or in additionally include one or more ribs or internal supports 312 located within the sealed chamber 355 of the lens body 305. The internal supports 312 can act to mechanically isolate the optical components of the lens from optical distortion during movement of the moving parts of the AIOL 300. In some implementations, the one or more internal supports 312 connect the anterior and posterior supports. In some implementations, a first surface of the internal support 312 can be coupled to a perimeter region of the shape changing membrane 345 (best shown in FIGS. 26B and 26C) or an anterior support defining the diameter of the shape changing membrane 345. In some implementations, the internal support 312 is additionally coupled to the static element 350 (or static lens) such that the internal support 312 is coupled on a first surface to a perimeter region of the shape changing membrane 345 and coupled on a second, opposite surface to a perimeter region of the static element 350 (see FIGS. 27A-27D). In either implementation (i.e. coupled to one or both of the anterior and posterior surfaces), at least a portion of the internal support 312 is separated a distance from the shape deformation membrane 340 such that the internal support 312 partitions the sealed chamber 355 into a deformable region 307 and a central region 303 within which optical fluid is contained. If the internal support 312 is coupled to just the shape changing membrane 345, a channel 342 can extend under the internal support 312 allowing for fluid communication between the deformable region 307 and the central region 303 of the sealed chamber 355 (best shown in FIG. 26B). If the internal support 312 is coupled to both the shape changing membrane 345 and the static element 350, one or more channels 342 can extend through the internal support 312 itself to allow for fluid communication between the deformable region 307 and the central region 303 of the sealed chamber 355 (best shown in FIG. 27B). The one or more channels 342 can include a cylindrical bore that extends from a region of an outer wall through to a region of an inner wall of the internal support 312. It should be appreciated that the channels 342 can have any of a variety of shapes and sizes. Alternatively, a plurality of internal supports 312 can be contained within the sealed chamber 355 that are spaced apart from one another creating one or more channels 342 between them for fluid communication within the sealed chamber 355 between the deformable region 307 and the central region 303 of the sealed chamber. The AIOLs described herein can incorporate 1, 2, 3, 4, 5 or more internal supports 312 within the sealed chamber 355.

During accommodation, inward/anterior movement of the ciliary structure can be harnessed by contact portions 335 of the force translation arms 315 causing the force translation arms 315 to move inward toward the optical axis A. Inward movement of the force translation arms 315 urges the shape deformation membrane 340 to undergo movement or deformation relative to the shape changing membrane 345, for example, towards the optical axis. Inward movement, collapse, compression or deformation of the deformable regions 307 of the shape deformation membrane 340 toward the optical axis causes the non-compressible optical fluid contained within the fixed volume, sealed chamber 355 to press against the surfaces of the sealed chamber 355 including the inner surface of the shape changing membrane 345. The shape changing membrane 345 can have a region surrounding the optical axis configured to bow outward or flex upon application of a force into a more spherical or convex shape in the optic zone thereby increasing the power of the lens for near vision focus without imposing stress or squeezing on the optic zone. The pressure of the optical fluid against the shape changing membrane 345 reshapes the outer surface. It should be appreciated that this shape change can occur without flow of fluid from one part of the lens body 305 to another. Rather, the compression of the fixed volume sealed chamber 355 (and deformable region 307) filled with non-compressible optical fluid drives the shape change of the membrane 345. The deformable region 307 and central region 303 of the sealed chamber 355 can both be within the optic zone such that deformation of the shape deformation membrane 340 (and the deformable region 307) occurs inside the optic zone. Alternatively, the deformable region 307 can be located outside the optic zone such that deformation of the shape deformation membrane 340 (and the deformable region 307) occurs outside the optic zone.

The internal support 312 can have a tapered geometry such that the supports 312 do not come into contact with moving parts of the lens such as the shape deformation membrane 340. For example as shown in 26C, the support 312 can have a wider dimension near where the support 312 couples with the shape changing membrane 345 and an outer wall that tapers away from the shape changing membrane 345 such that the support 312 has a narrower dimension near where the shape deformation membrane 340 deforms to the greatest degree during accommodation. In another example as shown in FIG. 27D, the support 312 can have a wider dimension on both anterior and posterior ends of the AIOL 300 where the support 312 couples with the shape changing membrane 345 and the static element 350, respectively, that tapers towards a center region. In this implementation, the support 312 forms a tapered spool shape.

The dimensions of the components of the devices described herein can vary. The devices can be configured to be implanted through an incision that is less than about 4 mm. In some implementations, the overall diameter of the device is approximately 8 mm, although this can vary. For example, a device having flexible or foldable stabilization haptics can have a first diameter during implantation that is smaller than the diameter it achieves after implantation following unfolding or expansion of the stabilization haptics. In some implementations, the exterior support can be made from a flexible material(s) such that the exterior support can bend during implantation of the device. In some implementations, the central, optic zone portion of the lens body can have a diameter that is about 2.5 mm, about 3.0 mm, about 3.5 mm, about 4.0 mm, about 4.5 mm, about 5.0 mm, about 5.5 mm, about 6.0 mm, about 6.5 mm, or greater diameter. In some implementations, the accommodating diameter, or the region of the central optic zone that undergoes a shape change, is greater than 3.0 mm.

As described above, the deformable regions of the lens body can move or collapse relative to the central region of the lens body upon application of a degree of force on the shape changing membrane. The force applied to achieve movement of the shape changing membrane of the lens body to effect accommodation can be as low as about 0.1 grams of force (go. In some implementations, the force applied can be between about 0.1 gf to about 5.0 gf or between about 0.5 gf to about 1.5 gf or between about 1.0 gf to about 1.5 gf. The movements of the deformable regions of the lens body relative to the central portion of the lens body in response to forces applied to achieve accommodation can be as small as about 50 um. The movements of the deformable regions of the lens body relative to the central portion of the lens body (or e.g. region 107 relative to central region 103 or the deformable portion 182 of the shape deformation membrane 140 relative to the central portion 180 of the shape deformation membrane 140) in response to forces applied can be between about 50 um to about 500 um, between about 50 um to about 150 um, or between about 100 um to about 150 um. These ranges of forces applied and that result in these ranges of movement can provide the devices described herein with an accommodating capability that is within a dynamic range of greater than 3 D. In some implementations, the power is between 4 D and 6 D for about 100-150 um movement. The devices described herein can have an accommodating range that is at least 3 D for about 100 um movement of the shape changing membrane and about a force of at least 0.1 gf applied to the shape changing membrane. In other implementations, the devices can have an accommodating range that is at least 3 D for about 50 um movement and at least about 1.0 gf.

Suitable materials or combinations of materials for the preparation of the various components of the devices disclosed herein are provided throughout. It should be appreciated that other suitable materials are considered. U.S. Patent Publication Nos. 2009/0234449, 2009/0292355 and 2012/0253459, which are each incorporated by reference herein in their entirety, provide further examples of other materials suitable for forming certain components for the devices described herein.

The various devices described herein can be implanted according to a variety of surgical methods known in the art. Depending upon the features and components of the device, they can be implanted using various techniques or using various implements. The devices described herein can be used alone or in combination with another intraocular lens or the patient's natural lens. As described herein the power of the lens body as well as the relative position of the force translation arms and/or stability haptics can be adjusted and/or fine-tuned prior to implantation, during implantation or any time after implantation. It should also be appreciated that the devices described herein can be inserted through a small incision, such as an incision that is no greater than 3.5 mm. The devices described herein can be implanted such that the device is positioned outside the lens capsule, for example anterior to the capsule and posterior to the iris. The devices described herein can be implanted such that the central portion of the lens body is aligned with the optical axis of the eye. The force translation arms can be positioned relative to the one or more ciliary structures such as the ciliary body or the ciliary muscle. The force translation arms can be positioned such that they abut with the ciliary structure (or very closely associated to the ciliary structure without abutting) without causing compression of the lens body including the deformable region of the lens body when the ciliary structure is in the resting, disaccommodated state (unaccommodated). However, the force translation arms can be positioned close enough to the ciliary structure such that upon contraction of the ciliary muscle the lens body undergoes accommodation and upon relaxation of the ciliary muscle the lens body undergoes disaccommodation and the materials of the lens body rapidly return to their resting state. The relative position and length of the force translation arms can be adjusted according to the various methods described above using one or more of the various features for adjustment described herein. The stabilization haptics can be positioned within the ciliary sulcus (or other region) to further stabilize the device within the eye. The resting power of the lens body can also undergo further adjustment and fine-tuning according to the various methods described herein and using one or more of the various features for power adjustment described herein.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. An accommodating intraocular lens device for treatment of an eye, the device comprising:
    an optical, lens body having a sealed chamber containing a fixed volume of optical fluid, the lens body comprising:
        an anterior lens element comprising a perimeter region and a central surface surrounded by the perimeter region, the central surface configured to outwardly bow;
        an annular support coupled to the perimeter region of the anterior lens element, the annular support having a shape deformation membrane extending along an arc of the annular support, the shape deformation membrane configured to undergo displacement relative to the perimeter region of the anterior lens element;
        a static, posterior lens element positioned opposite the anterior lens element;
        an immovable, internal support encircling the central surface of the anterior lens element, wherein the immovable, internal support has an anterior-facing surface coupled to the perimeter region of the anterior lens element and has an anterior-to-posterior thickness; and
        the fixed volume of optical fluid,
        wherein an inner surface of the anterior lens element, an inner surface of the shape deformation membrane and an inner surface of the static, posterior lens element collectively form the sealed chamber of the lens body containing the fixed volume of optical fluid;
    a force translation arm having a first end configured to contact an outer surface of the shape deformation membrane of the lens body and a free end available and configured to engage a ciliary structure of the eye outside the capsular bag when the lens device is implanted in the eye such that an optical axis of the lens body is substantially aligned with a visual axis of the eye,
    wherein the force translation arm is movable relative to the lens body and the immovable, internal support to cause inward movement of the shape deformation membrane; and
    a stabilization haptic coupled to the lens body.

2. The device of claim 1, wherein the anterior-to-posterior thickness of the immovable, internal support tapers towards the shape deformation membrane such that the anterior-to-posterior thickness at an outer edge of the immovable, internal support is less than the anterior-to-posterior thickness away from the outer edge.

3. The device of claim 1, wherein inward movement of the force translation arm causes the inward movement of the shape deformation membrane causing a deformation of the sealed chamber.

4. The device of claim 1, wherein inward movement of the shape deformation membrane causes the optical fluid in the sealed chamber to press against the inner surface of the anterior lens element.

5. The device of claim 1, wherein the immovable, internal support mechanically isolates optical components of the lens body from distortion during movement of the force translation arm relative to the lens body.

6. The device of claim 1, wherein the immovable, internal support comprises a plurality of immovable, internal supports spaced apart from one another within the sealed chamber.

7. The device of claim 2, wherein the anterior-to-posterior thickness at the outer edge prevents contact between the immovable, internal support and the shape deformation membrane during inward movement of the shape deformation membrane.

8. The device of claim 1, wherein the stabilization haptic is bonded to the lens body.

9. The device of claim 1, wherein the stabilization haptic is molded as part of the lens body.

10. The device of claim 1, wherein the immovable, internal support forms a partition within the sealed chamber dividing the sealed chamber into a deformable region and a central region.

11. The device of claim 10, wherein the deformable region is located inside an optic zone of the lens body.

12. The device of claim 10, wherein inward movement of the shape deformation membrane deforms the deformable region.

13. The device of claim 1, wherein inward movement of the shape deformation membrane compresses the sealed chamber.

14. The device of claim 1, wherein the optical fluid in the sealed chamber is non-compressible and presses against the inner surface of the anterior lens element upon inward movement of the shape deformation member outward bowing of the anterior lens element.

15. The device of claim 1, wherein the immovable, internal support is further coupled to a region of the static, posterior lens element.

16. The device of claim 10, wherein the immovable, internal support comprises a channel extending through the internal support providing fluid communication between the deformable region and the central region of the sealed chamber.

* * * * *